(12) United States Patent
Backes et al.

(10) Patent No.: US 11,535,584 B2
(45) Date of Patent: Dec. 27, 2022

(54) HOMOVANILLINIC ACID ESTER, IN PARTICULAR FOR CREATING A WARM AND/OR PUNGENT SENSATION

(71) Applicant: SYMRISE AG, Holzminden (DE)

(72) Inventors: Michael Backes, Holzminden (DE); Jakob Peter Ley, Holzminden (DE); Andreas Degenhardt, Berkshire (GB); Susanne Paetz, Höxter (DE); Katharina Reichelt, Holzminden (DE); Thomas Riess, Holzminden (DE); Bettina Klose, Braunschweig (DE); Fabia Hentschel, Holzminden (DE)

(73) Assignee: SYMRISE AG, Holzminden (DE)

( * ) Notice: Subject to any disclaimer, the term of this patent is extended or adjusted under 35 U.S.C. 154(b) by 2 days.

(21) Appl. No.: 17/077,133

(22) Filed: Oct. 22, 2020

(65) Prior Publication Data

US 2021/0040028 A1      Feb. 11, 2021

Related U.S. Application Data

(63) Continuation of application No. 16/345,921, filed as application No. PCT/EP2015/058004 on Apr. 14, 2015, now abandoned.

(30) Foreign Application Priority Data

Apr. 16, 2014   (EP) .................................... 14165020

(51) Int. Cl.
| | |
|---|---|
| *C07C 69/734* | (2006.01) |
| *A23L 27/20* | (2016.01) |
| *A23L 27/00* | (2016.01) |
| *A61K 47/14* | (2017.01) |
| *C07C 69/708* | (2006.01) |
| *C07C 69/757* | (2006.01) |
| *A23B 4/06* | (2006.01) |

(52) U.S. Cl.
CPC .............. *C07C 69/734* (2013.01); *A23B 4/06* (2013.01); *A23L 27/204* (2016.08); *A23L 27/2052* (2016.08); *A23L 27/84* (2016.08); *A23L 27/88* (2016.08); *A61K 47/14* (2013.01); *C07C 69/708* (2013.01); *C07C 69/757* (2013.01); *A23V 2002/00* (2013.01); *A23V 2200/15* (2013.01); *A23V 2200/16* (2013.01); *C07C 2601/14* (2017.05)

(58) Field of Classification Search
None
See application file for complete search history.

(56) References Cited

U.S. PATENT DOCUMENTS

| | | |
|---|---|---|
| 2009/0258128 A1 | 10/2009 | Saito et al. |
| 2012/0093742 A1 | 4/2012 | Kaouas et al. |

FOREIGN PATENT DOCUMENTS

| | | |
|---|---|---|
| WO | 03/106404 A1 | 12/2003 |

OTHER PUBLICATIONS

MacNamaraetal (S Afr J Enol Vitic 11:82-92, 2001) (Year: 2001).*
Cabaroglu et al (Enzyme and Microbial Tech 33:581-587, 2003) (Year: 2003).*
Korean Office Action and English translation dated Oct. 28, 2021 for corresponding Korean Application No. 10-2016-7032034.
International Search Report and Written Opinion dated Jul. 7, 2015 for corresponding PCT Application No. PCT/EP2015/058004.
International Preliminary Report on Patentability dated Oct. 18, 2016 for corresponding PCT Application No. PCT/EP2015/058004.
Szolcsanyi, J. et al., "Sensory Effects of Capsaicin Congeners. I. Relationship Between Chemical Structure and Pain-Producing Potency of Pungent Agents", Arzneimittel Forschung. Drug Research, vol. 25, No. 12, 1975, pp. 1877-1881 XP009073143.
Tao, G. et al., "Eugenol and its structural analogs inhibit monoamine oxidase A and exhibit antidepressant -like activity", Bioorganic & Medicianl Chemistry, vol. 13, No. 15, 2005, pp. 4777-4788 XP027637988.
Indian Office Action dated Dec. 23, 2019 for corresponding Indian Application No. 201637037838.
Delgado De La Torre et al., J. Sci. Food Agric., vol. 94; pp. 504-514, 2014 (published Jun. 21, 2013).
Philippines Office Action dated Aug. 26, 2020 for corresponding Philippines Application No. 1/2016/502050.

* cited by examiner

*Primary Examiner* — Craig D Ricci
(74) *Attorney, Agent, or Firm* — Polsinelli PC

(57) ABSTRACT

Compounds of formula (I) and novel uses of compounds of formula (I), such as for flavour compositions. New preparations and new methods using compounds of formula (I).

12 Claims, 3 Drawing Sheets

| German | English |
|---|---|
| Intensität | Intensity |
| mAU | mAU |
| EHV | EHV |
| UV | UV |
| Zeit | Time |

| German | English |
|---|---|
| mAU | mAU |
| Minuten | minutes |
| EHV | EHV |

HOMOVANILLINIC ACID ESTER, IN PARTICULAR FOR CREATING A WARM AND/OR PUNGENT SENSATION

CROSS-REFERENCE TO RELATED APPLICATIONS

This application is a continuation application of U.S. application Ser. No. 16/345,921, filed Apr. 29, 2019, which is a national stage application (under 35 U.S.C. § 371) of PCT/EP2015/058004, filed Apr. 14, 2015, which claims benefit of priority of European Application No. 14165020.0, filed Apr. 16, 2014, which are incorporated herein by reference in their entireties.

FIELD OF THE INVENTION

The present invention particularly relates to novel uses of compounds of formula (I) (as described herein), partly also of novel compounds of formula (I) as such, aroma compositions containing compounds of formula (I), new preparations as well as new methods using compounds of formula (I). Further aspects of the present invention arise from the patent claims and the following description including examples.

BACKGROUND OF THE INVENTION

Capsaicin [N-(4-hydroxy-3-methoxybenzyl)-8-methyl-(6E)-nonenoic acid amide] and other capsaicinoids such as nonivamide ([N-(4-hydroxy-3-methoxybenzyl)-nonanoic acid amide) have been known for a long time as pungent and spicy flavours from different *capsicum* species, in particular, chili pepper. At an appropriately low dosage of capsaicinoids, a neutral pungency and a warm sensation is perceived in the mouth, wherein the threshold for pain-inducing pungency and hot sensation is exceeded very quickly. However, the use of capsaicin in food is not allowed in the European Union (was deleted from the Community Flavouring List in 2004), since evaluation of the genotoxic potential of the compound yielded a negative result (European Food Safety Authority (EFSA), P., Italy, Opinion of the Scientific Committee on Food on Capsaicin. *European Commission* 2002, (SDF/CS/FLAV/FLAVOUR/8 ADD1 Final). Moreover, use in foods is often difficult, since capsaicin has a very low taste threshold and a high potency as a pungent substance (16,000,000 Scoville units, cf. http://en.wikipedia.org/wiki/Capsaicin; version of the record as last amended on 11 Nov. 2011, 9:02 pm). Moreover, due to the high price of the pure substance, capsaicin is used almost exclusively in the form of *capsicum* extract, which contains residues of other flavouring substances, which taste or smell like *Capsicum*, besides other pungent substances and is, therefore, only limitedly suitable for broad use. Thus, there is a need for less problematic pungent substances despite the good sensory properties.

Although the piperine (1-piperoyl piperidine) that occurs in white pepper also causes a strongly pungent sensation (Römpp Lexicon Chemistry of Natural Compounds, Thieme 1997, p. 500) it has a relative pungency of only about 1% as compared to capsaicin. Furthermore, piperine has an intense taste of its own, reminiscent of pepper, so that the use in many preparations can only occur to a limited extent.

Due to the lipophilic nature of these pungent vanilloid substances, the onset of the pungent sensation often is delayed by a few seconds and also persists for a particularly long time, especially in preparations containing weakly lipophilic components (e.g. triglycerides), wherein at the same time the solubility is only insufficient. The same applies to pungent substances such as gingerol-[6] from ginger or paradol-[6] from grains of paradise, both of which have a pungent taste, but have a strong aftertaste.

Other (e.g. Starkenmann, C.; Cayeux, I.; Birkbeck, A. A., Exploring Natural Products for New Taste Sensations. *Chimia* 2011, 65, (6), 407-410) pungent-tasting substances such as the drimane, polygodial (from Tasmanian pepper, *Tasmannia lanceolata*) or resiniferatoxin from *Euphorbia resinifera* are known (Szallasi, A.; Biro, T.; Modarres, S.; Garlaschelli, L.; Petersen, M.; Klush, A.; Vidari, G.; Jonassohn, M.; De Rosa, S.; Sterner, O.; Blumberg, P. M.; Krause, J. E., Dialdehyde sesquiterpenes and other terpenoids as vanilloid. *Eur. J. Pharmacol.* 1998, 356, 81-89), but the drimanes are limited in their use due to their dialdehyde structure, since they react with free amino groups of, e.g. proteins and thus lose their effect and resiniferatoxin is highly toxic and unsuitable for human diet. Moreover, these substances are also strongly lipophilic.

The methyl ester of homovanillic acid was determined in various woods, which are used for storing wine and spirits (e.g. Fernandez de Simon, B.; Esteruelas, E.; Munoz, A. M.; Cadahia, E.; Sanz, M., *J. Agric. Food Chem.* 2009, 57, 3217-3227.). In contrast, the ethyl ester of homovanillic acid was detected in wine and spirits themselves, mostly in connection with a storage in oak barrels (e. g. Cabaroglu, T.; Canbas, A.; Baumes, R.; Bayonove, C.; Lepoutre, J. P.; Günata, Z., *J. Food Sci.* 1997, 62, 680-692. van Jaarsveld, F. P.; Hattingh, S.; Minnaar, P., S. *Afr. J. Enol. Vitic.* 2009, 30, 24-37.). However, the low concentrations of e.g. 2 μg/L are not sufficient to cause a warm and/or pungent effect.

US 2009/0170942 A1 discloses specific ester derivatives of homovanillinic acid and various (medical) applications thereof.

In a study of pain sensation towards different capsaicin derivatives in rat eyes, methyl, propyl, octyl, nonyl and dodecyl esters of homovanillic acid were tested and assessed as being active (Szolcsanyi, J.; Jancso-Gabor, A., *Arzneim.-Forsch.* (*Drug. Res.*) 1975, 25, 1877-1881).

Unlike the aforementioned pungent substances, ethanol is a small hydrophilic molecule, which causes a fast and pleasant pungent sensation that does not last very long. Since this only works at relatively high concentrations of 0.5% or more, but the consumption of ethanol causes health disorders and may also result in addiction upon prolonged consumption, flavour formulations, which can simulate the pungency profile of ethanol, without posing the disadvantages mentioned are sought after. Some pungent substances have already been described for this application, for instance, EP 1,515,943 B1 describes specific longer-chain vanillylmandelic acid alkylamides or WO 2009 065,239 describes polygodial and warburganal as pungent substances to obtain an ethanol-like pungent sensation; long-lasting pungent sensation, which is not described by the testers as sensation typical of ethanol is again observed due to the lipophilicity.

DETAILED DESCRIPTION OF THE INVENTION

Figure 1:
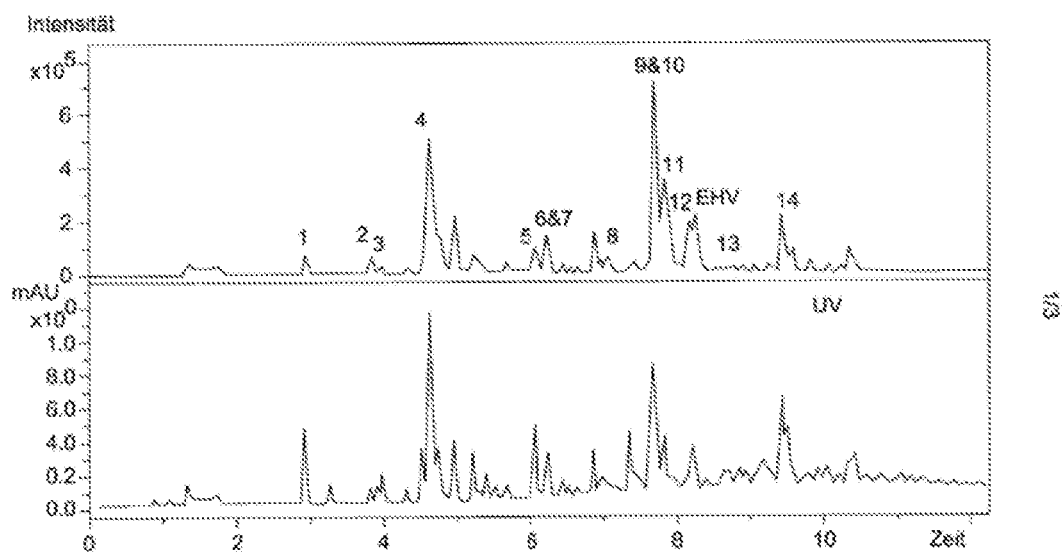
FIG. 1 is a chromatogram graph of the compounds from the primary reaction mixture containing ethyl homovanillate by reaction of ascorbic acid with vanillyl alcohol after 6 h at 100° C. according to aspects of the invention.

Thus, there is the need for less lipophilic, quickly sensorially onsetting and not long-lasting pungent substances that create a warming taste sensation. There is special need for substances that possess the above-mentioned properties and occur naturally or are formed in usual food processes from naturally occurring food components or flavourings.

This need can now be met according to the invention by using a compound of formula (I)

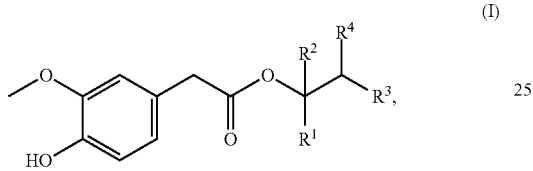

wherein
(i) $R^1$ and $R^2$ represent, independently of each other, a hydrogen atom or an alkyl residue with 1-2 carbon atoms,
$R^3$ and $R^4$ represent, independently of each other, a hydrogen atom or a linear or branched alkyl residue with 1 to 5 carbon atoms (for example, selected from the group consisting of methyl, ethyl, 1-propyl, 2-propyl, 1-butyl, 2-butyl, tert-butyl, 2-methylprop-1-yl, 1-, 2- or 3-pentyl, 2-methylbut-1-yl, 2-methylbut-2-yl, 3-methylbut-1-yl and 3-methylbut-2-yl, preferably of methyl, ethyl, 1-propyl, 2-propyl, 1-butyl, 2-butyl, tert-butyl, 2-methylprop-1-yl and 1-pentyl), a phenyl residue, an alkylphenyl residue or a phenylalkyl residue or a linear or branched alkenyl residue with 2 to 4 carbon atoms (for example, selected from the group consisting of ethenyl, prop-2-en-1-yl, prop-1-en-1-yl, prop-1-en-2-yl, 1- or 2-cyclopropenyl, but-1-en-1-yl, but-1-en-2-yl, but-1-en-3-yl, but-2-en-1-yl, but-3-en-1-yl, but-2-en-2-yl, 2-methylprop-1-en-1-yl, 2-methylprop-2-en-1-yl, 1,3-butadien-1-yl, 1,3-butadien-2-yl, and the respective possible Z and E-isomers, if applicable) or an alkenylphenyl residue or a phenylalkylene residue,
or
(ii) $R^1$ and $R^3$ along with the carbon atoms linking them form a cyclohexyl ring (the residues $R^2$ and $R^4$ are substitutes of the cycloalkyl ring; refer to, in this regard, e.g. formula (a) further below), which optionally is substituted with an additional residue $R^5$, wherein $R^5$ is an alkyl residue with 1-2 carbon atoms, $R^2$ represents a hydrogen atom or an alkyl residue with 1-2 carbon atoms,
$R^4$ represents a hydrogen atom or a linear or branched alkyl residue with 1 to 5 carbon atoms (for example, selected from the group consisting of methyl, ethyl, 1-propyl, 2-propyl, 1-butyl, 2-butyl, tert-butyl, 2-methylprop-1-yl, 1-, 2- or 3-pentyl, 2-methylbut-1-yl, 2-methylbut-2-yl, 3-methylbut-1-yl and 3-methylbut-2-yl, preferably of methyl, ethyl, 1-propyl, 2-propyl, 1-butyl, 2-butyl, tert-butyl, 2-methylprop-1-yl and 1-pentyl), a phenyl residue, an alkylphenyl residue or a phenylalkyl residue or a linear or branched alkenyl residue with 2 to 4 carbon atoms (for example, selected from the group consisting of ethenyl, prop-2-en-1-yl, prop-1-en-1-yl, prop-1-en-2-yl, 1- or2-cyclopropenyl, but-1-en-1-yl, but-1-en-2-yl, but-1-en-3-yl, but-2-en-1-yl, but-3-en-1-yl, but-2-en-2-yl, 2-methylprop-1-en-1-yl, 2-methylprop-2-en-1-yl, 1,3-butadien-1-yl, 1,3-butadien-2-yl, and the respective possible Z and E-isomers, if applicable) or an alkenylphenyl residue or a phenylalkylene residue, or of a physiologically acceptable salt thereof, wherein the phenolic hydroxy group in formula (I) is deprotonated, or of a mixture comprising one or several compounds of formula (I) and/or physiologically acceptable salts thereof (in particular, its sodium, potassium, ammonium, calcium, magnesium or zinc salts), wherein the phenolic hydroxy group in formula (I) is deprotonated, respectively, or consisting of a plurality of different compounds of formula (I) and/or salts thereof, wherein the phenolic hydroxy group in formula (I) is deprotonated, respectively, as flavouring.

In the case of a mixture of different compounds of formula (I) (as described herein), it applies within the scope of the present text that the different compounds may, for example, not only be compounds with different molecular formula, but also different stereoisomers with identical molecular formula.

The compounds of formula (I) described herein are suitable, in particular,
  as flavouring and/or pungent substance that creates a warm and/or pungent effect, i.e. as a substance that can sensorially create a warm sensation,
  and/or
  as flavouring for reducing or masking an unpleasant taste sensation, preferably selected from the group consisting of astringent, bitter, dry, dusty, floury, chalky and metallic (more details hereto arise from the descriptions further below),
  and/or
  as flavouring for increasing a pleasant taste sensation, preferably selected from the group consisting of warming, pungent and cooling (more details hereto arise from the descriptions further below).

At this point, it should be noted that the advantages and effects of the compounds of formula (I) described herein usually accordingly apply to their salts (as described herein).

Use as described above is preferred, wherein the following applies to the compound of formula (I) and/or one, several or all of the compounds of formula (I), independently of each other, in the mixture:
  (i) $R^1$ and $R^2$ represent, independently of each other, a hydrogen atom or methyl,
    $R^3$ and $R^4$ represent, independently of each other, a hydrogen atom or a linear or branched alkyl residue with 1 to 5 carbon atoms or a phenyl residue, an alkylphenyl residue or a phenylalkyl residue or an alkenylphenyl residue or a phenylalkenyl residue (e.g. as described above), or (ii) Formula (I) corresponds to the following formula (a)

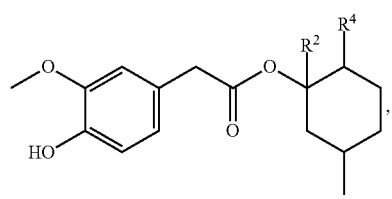
(Ia)

R² represents a hydrogen atom,

R⁴ represents 2-propyl.

Use as described above is also preferred, wherein the following applies to the compound of formula (I) and/or one, several or all of the compounds of formula (I), independently of each other, in the mixture:

R¹ and R² represent a hydrogen atom, respectively,

R³ represents a hydrogen atom or a linear or branched alkyl residue with 1 to 4 carbon atoms or a phenyl residue, an alkylphenyl residue or phenylalkyl residue or an alkenylphenyl residue or a phenylalkenyl residue, R⁴ represents a hydrogen atom.

Particularly preferred is the compound of formula (I) and/or one, several or all compounds of the formula (I) in the mixture selected or from the group consisting of

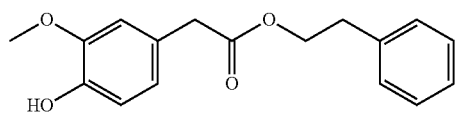
2-phenylethyl-2-(4-hydroxy-3-methoxyphenyl) acetate (1)

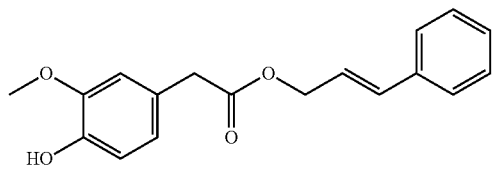
[(E)-cinnamyl]-2-(4-hydroxy-3-methoxyphenyl) acetate (2)

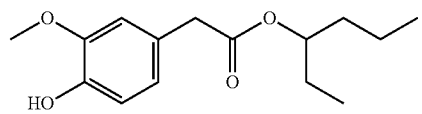
1-ethylbutyl-2-(4-hydroxy-3-methoxyphenyl) acetate (3)

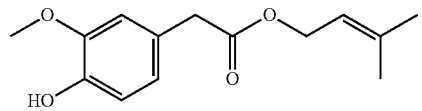
3-methylbut-2-enyl-2-(4-hydroxy-3-methoxyphenyl) acetate (4)

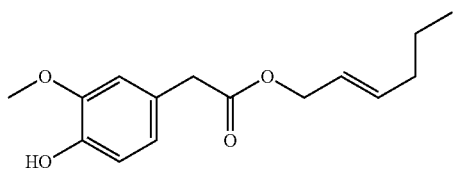
[(E)-hex-2-enyl]-2-(4-hydroxy-3-methoxyphenyl) acetate (5)

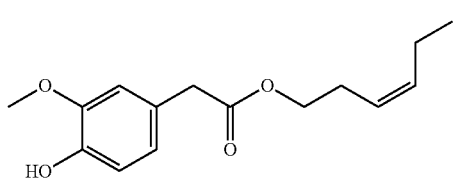
[(Z)-hex-3-enyl]-2-(4-hydroxy-3-methoxyphenyl) acetate (6)

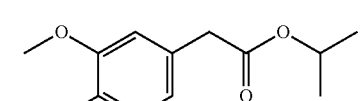
isopropyl-2-(4-hydroxy-3-methoxy-phenyl) acetate (7)

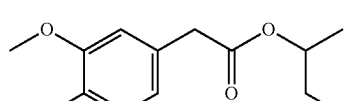
sec-butyl-2-(4-hydroxy-3-methoxyphenyl) acetate (8)

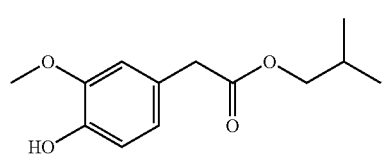
isobutyl-2-(4-hydroxy-3-methoxy-phenyl) acetate (9)

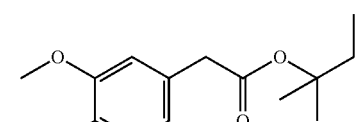
1,1-dimethylpropyl 2-(4-hydroxy-3-methoxyphenyl) acetate (10)

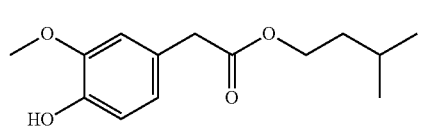
isopentyl-2-(4-hydroxy-3-methoxyphenyl) acetate (11)

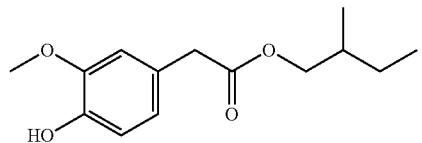
2-methylbutyl-2-(4-hydroxy-3-methoxyphenyl) acetate (12)

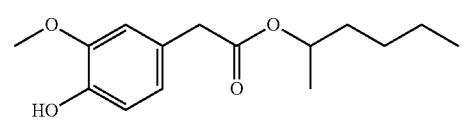
1-methylpentyl-2-(4-hydroxy-3-methoxyphenyl) acetate (13)

heptyl-2-(4-hydroxy-3-methoxyphenyl) acetate (14)

1-methylhexyl-2-(4-hydroxy-3-methoxyphenyl) acetate (15)

(2-isopropyl-5-methyl-cyclohexyl)-2-(4-hydroxy-3-methoxyphenyl) acetate (16)

ethyl-2-(4-hydroxy-3-methoxyphenyl) acetate (17)

propyl-2-(4-hydroxy-3-methoxyphenyl) acetate (18)

butyl-2-(4-hydroxy-3-methoxyphenyl) acetate (19)

pentyl-2-(4-hydroxy-3-methoxyphenyl) acetate (20)

hexyl-2-(4-hydroxy-3-methoxyphenyl) acetate (21)

3-phenylpropyl 2-(4-hydroxy-3-methoxyphenyl) acetate (22)

4-phenylbutyl 2-(4-hydroxy-3-methoxyphenyl) acetate (23)

The compounds described herein are advantageously suitable for use (in particular, as described above) in a pharmaceutical preparation, a preparation serving nutrition, oral hygiene, or pleasure, preferably wherein the total quantity of compound(s) of formula (I) and/or salt(s) thereof in the preparation is sufficient to
(a) sensorially create a warming and/or pungent effect on the tongue or in the oral cavity when used or consumed, and/or
(b) reduce or mask an unpleasant taste sensation, preferably selected from the group consisting of astringent, bitter, dry, dusty, floury, chalky and metallic (more details hereto arise from the descriptions further below),
and/or
(c) increase a pleasant taste sensation, preferably selected from the group consisting of warming, pungent and cooling (more details hereto arise from the descriptions further below).

It is preferred according to a particular aspect of the present invention when the total amount of compound(s) of the formula (I) and/or salt(s) thereof in the preparation is not sufficient to create a warming or pungent effect on the tongue or in the oral cavity, but is sufficient to mask or reduce an unpleasant taste sensation of an unpleasant tasting substance or mixture of substances.

Another aspect of the present invention relates to new compounds of the formula (I), salts thereof, their mixtures, namely a compound of the formula (I) or a physiologically acceptable salt thereof, wherein the phenolic hydroxy group in formula (I) is deprotonated, or a mixture comprising one or several different compounds of formula (I) and/or one or several physiologically acceptable salts thereof, wherein the phenolic hydroxy group in formula (I) is deprotonated, respectively, or consisting of a plurality of different compounds of formula (I) and/or physiologically acceptable salts thereof, wherein the phenolic hydroxy group in formula (I) is deprotonated, respectively, (I)

wherein
(i) $R^1$ and $R^2$ represent, independently of each other, a hydrogen atom or an alkyl residue with 1-2 carbon atoms,
$R^3$ and $R^4$ represent, independently of each other, a hydrogen atom or a linear or branched alkyl residue with 1 to 5 carbon atoms (e.g. as described above), a phenyl residue, an alkylphenyl residue or a phenylalkyl residue or a linear or branched alkenyl residue with 2 to 4 carbon atoms (e.g. as described above) or an alkenylphenyl residue or a phenylalkenyl residue, or (ii) $R^1$ and $R^3$ along with the carbon atoms linking them form a cyclohexyl ring, which optionally is substituted with an additional residue $R^5$, wherein $R^5$ is an alkyl residue with 1-2 carbon atoms, $R^2$ represents a hydrogen atom or an alkyl residue with 1-2 carbon atoms, $R^4$ represents a hydrogen atom or a linear or branched alkyl residue with 1 to 5 carbon atoms (e.g. as described above), a phenyl residue, an alkylphenyl residue or a phenylalkyl residue or a linear or branched alkenyl residue with 2 to 4 carbon atoms (e.g. as described above) or an alkenylphenyl residue or a phenylalkenyl residue, provided that $R^1$, $R^2$, $R^3$ and $R^4$ do not all represent hydrogen atoms, and in case $R^1$, $R^2$ and $R^4$ represent hydrogen, $R^3$ neither stands for a linear alkyl residue with 1, 2, 4 or 5 carbon atoms (corresponding alkenyl residues are not excluded) nor 2-propyl or phenyl, preferably also not phenylmethyl or methylphenyl, and in case $R^2$, $R^3$ and $R^4$ represent hydrogen, $R^1$ does not represent a linear alkyl residue with 1 or 2 carbon atoms, $R^3$ and $R^4$ do not represent methyl, if $R^1$ and $R^2$ represent hydrogen, preferably neither $R^3$ nor $R^4$ represent methyl, if $R^1$ and $R^2$ represent hydrogen, and $R^1$ and $R^2$ do not represent methyl, if $R^3$ and $R^4$ represent hydrogen, preferably neither $R^1$ nor $R^2$ represent methyl, if $R^3$ and $R^4$ represent hydrogen.

It is particularly preferred when the compound of formula (I) and/or one, several or all compounds of the formula (I) in the mixture are selected or from the group consisting of

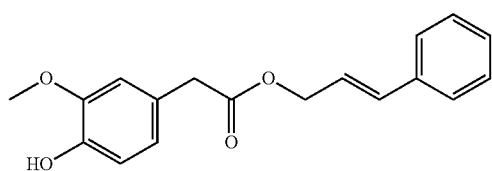

[(E)-cinnamyl]-2-(4-hydroxy-3-methoxyphenyl) acetate (2)

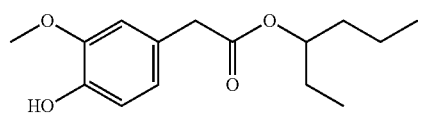

1-ethylbutyl-2-(4-hydroxy-3-methoxyphenyl) acetate (3)

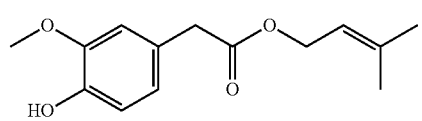

3-methylbut-2-enyl-2-(4-hydroxy-3-methoxyphenyl) acetate (4)

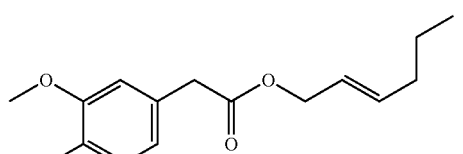

[(E)-hex-2-enyl]-2-(4-hydroxy-3-methoxyphenyl) acetate (5)

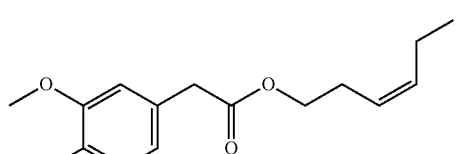

[(Z)-hex-3-enyl]-2-(4-hydroxy-3-methoxyphenyl) acetate (6)

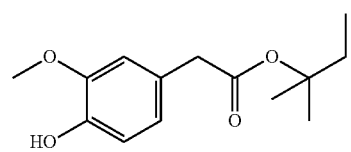

1,1-dimethylpropyl 2-(4-hydroxy-3-methoxyphenyl) acetate (10)

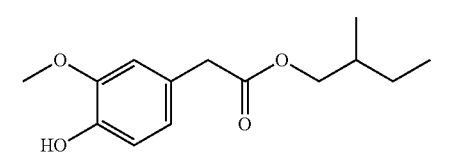

2-methylbutyl-2-(4-hydroxy-3-methoxyphenyl) acetate (12)

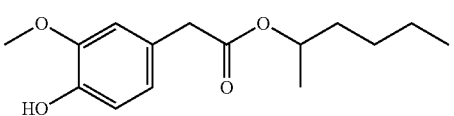

1-methylpentyl-2-(4-hydroxy-3-methoxyphenyl) acetate (13)

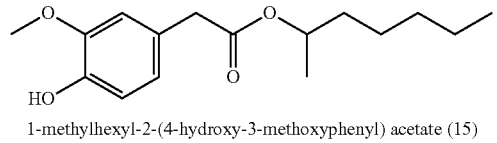

1-methylhexyl-2-(4-hydroxy-3-methoxyphenyl) acetate (15)

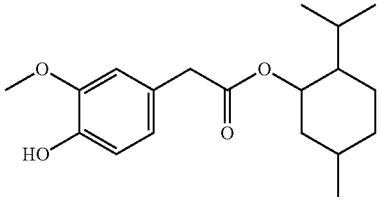

(2-isopropyl-5-methyl-cyclohexyl)-2-(4-hydroxy-3-methoxyphenyl) acetate (16)

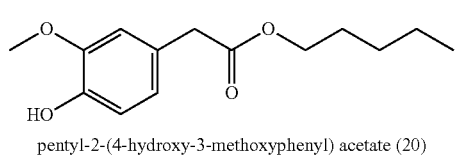

pentyl-2-(4-hydroxy-3-methoxyphenyl) acetate (20)

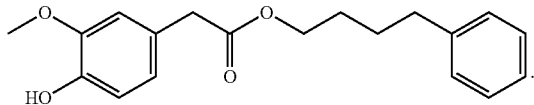

4-phenylbutyl 2-(4-hydroxy-3-methoxyphenyl) acetate (23)

Apart from that, what has been stated in connection with the compounds, salts and mixtures to be used according to the invention applies accordingly to the novel compounds of formula (I) and their salts as well as mixtures thereof.

In the context of the present invention, it has been found that compounds of the formula (I) or their salts and mixtures thereof, advantageously from concentrations of 0.1 mg/kg, particularly from 1.0 mg/kg, create quickly onsetting and little long-lasting, pleasant pungency or warming and slightly sharp sensations.

Accordingly, the present invention also relates, in particular, to novel flavour compositions, namely a flavour composition,
(A) comprising or consisting of a novel mixture according to the invention as described above,
preferably wherein
the total quantity of compound(s) of formula (I) and/or salt(s) thereof in the flavour composition is in the range of 100-100,000 mg/kg, preferably in the range of 250-40,000 mg/kg, particularly preferably in the range of 250 to 15,000 mg/kg, based on the total weight of the flavour composition
or
(B) comprising a compound of the formula (I), as defined above in connection with a use according to the invention, or a physiologically acceptable salt thereof, as defined above in connection with a use according to the invention, or comprising or consisting of a mixture as defined above in connection with a use according to the invention,
wherein
the total quantity of compound(s) of formula (I) and/or salt(s) thereof in the flavour composition is in the range of 100-100,000 mg/kg, preferably in the range of 250-40,000 mg/kg, particularly preferably in the range of 250 to 15,000 mg/kg, based on the total weight of the flavour composition,
preferably additionally comprising one or several further flavours, which do not correspond to the formula (I), for example selected from the group consisting of
a) warming or pungent substances, preferably selected from the list consisting of: capsaicinoids, such as for example, capsaicin, dihydrocapsaicin or nonivamide; gingerols, such as for example, gingerol-[6], gingerol-[8], or gingerol-[10]; shogaols such as shogaol-[6], shogaol-[8], shogaol-[10]; gingerdiones, such as for example gingerdione-[6], gingerdione-[8] or gingerdione-[10]; paradols such as for example paradol-[6], paradol-[8] or paradol-[10]; dehydrogingerdiones such as for example dehydrogingerdione-[6], dehydrogingerdione-[8] or dehydrogingerdione-[10]; piperine and piperine derivatives;
b) substances perceivable as pungent or biting, preferably selected from the group consisting of: aromatic isothiocyanates, such as for example, phenylethyl isothiocyanate, allyl isothiocyanate, cyclopropyl isothiocyanate, butyl isothiocyanate, 3-methylthiopropyl isothiocyanate, 4-hydroxybenzyl isothiocyanate, 4-methoxybenzyl isothiocyanate;
c) alkamides described as causing a tingling sensation, preferably selected from the group consisting of 2E,4E-decadienoic acid-N-isobutylamide (trans-pellitorine) (in particular, those as described in WO 2004/043906, which become part of this application by way of reference with respect to the corresponding compounds disclosed therein); 2E,4Z-decadienoic acid-N-isobutylamide (cis-pellitorine) (in particular, those as described in WO 2004/000787, which become part of this application by way of reference with respect to the corresponding compounds disclosed therein); 2Z,4Z-decadienoic acid-N-isobutylamide; 2Z,4E-decadienoic acid-N-isobutylamide; 2E,4E-decadienoic acid-N-([2S]-2-methylbutyl)amide; 2E,4E-decadienoic acid-N-([2S]-2-methylbutyl)amide; 2E,4E-decadienoic acid N-([2R]-2-methylbutylamide); 2E,4Z-decadienoic acid-N-(2-methylbutyl)amide; 2E,4E-decadienoicacid-N-piperide(achilleamide); 2E,4E-decadienoic acid-N-piperide (sarmentine); 2E-decenoic acid-N-isobutylamide; 3E-decenoic acid-N-isobutylamide; 3E-nonenoic acid-N-isobutylamide; 2E,6Z,8E-decatrienoic acid-N-isobutylamide (spilanthol); 2E,6Z,8E-decatrienoic acid-N-([2S]-2-methylbutyl)amide (homo-spilanthol); 2E,6Z,8E-decatrienoic acid-N-([2R]-2-methylbutyl)amide; 2E-decen-4-yne-acid-N-isobutylamide; 2Z-decen-4-yne-acid-N-isobutylamide; 2E,6Z,8E,10E-dodecatetraenoic acid-N-(2-methylpropyl)amide (alpha-sanshool); 2E,6Z,8E,10E-dodecatetraenoic acid-N-(2-hydroxy-2-methylpropyl)amide (alpha-hydroxysanshool); 2E,6E,8E,10E-dodecatetraenoic acid-N-(2-hydroxy-2-methylpropyl) amide (gamma-hydroxysanshool); 2E,4E,8Z,10E,12E-tetradecapentaenoic acid-N-(2-hydroxy-2-methylpropyl)amide (gamma-hydroxysanshool); 2E,4E,8E,10E,12E-tetradecapentaenoic acid-N-(2-hydroxy-2-methylpropyl)amide (gamma-hydroxyisosanshool); 2E,4E,8Z,10E,12E-tetradecapentaenoic acid-N-(2-methyl-2-propenyl)amide (gamma-dehydrosanshool); 2E,4E,8Z,10E,12E-tetradecapentaenoic acid-N-(2-methylpropyl)amide (gamma-sanshool); 2E,4E,8Z,11Z-tetradecatetraenoic acid-N-(2-hydroxy-2-methylpropyl)amide (bungeanool); 2E,4E,8Z,11E-tetradecatetraenoic acid-N-(2-hydroxy-2-methylpropyl)amide (isobungeanool); 2E,4E,8Z-tetradecatrienoic acid-N-(2-hydroxy-2-methylpropyl)amide (dihydrobungeanool) and 2E,4E-tetradecadienoic acid-N-(2-hydroxy-2-methylpropyl) amide (tetrahydrobungeanool);
d) substances with physiological cooling effect, preferably selected from the following list: menthol and derivatives thereof (e.g. L-menthol, D-menthol, racemic menthol, isomenthol, neoisomenthol, neomenthol) menthyl ether (e.g. (L-menthoxy)-1,2-propanediol, (L-menthoxy)-2-methyl-1,2-propanediol, L-menthylmethyl ether), menthyl ester (e.g. menthyl formate, menthyl acetate, menthyl isobutyrate, menthyl lactate, L-menthyl-L-lactate, L-menthyl-D-lactate, menthyl-(2-methoxy) acetate, menthyl-(2-methoxyethoxy) acetate, menthyl pyroglutamate), menthyl carbonate (e.g. menthyl propylene glycol carbonate, menthyl ethylene glycol carbonate, menthyl glycerol carbonate or mixtures thereof), the half-esters of menthols with a dicarboxylic acid or derivatives thereof (e.g. mono-menthyl succinate, mono-menthyl glutarate, mono-menthyl malonate, O-menthyl succinic acid ester-N, N-(dimethyl)amide, O-menthyl succinic acid esteramide), menthane carboxamides other than those mentioned in the present invention (e.g. menthane carboxylic acid-N-ethylamide [WS3], menthane carboxylic acid-N-(p-methoxyphenyl)amide [SC1], Nα-(menthane carbonyl) glycine ethyl ester [WS5], menthane carboxylic acid-N-(4-cyanophenyl)amide, menthane carboxylic acid-N-(alkoxyalkyl)amides), menthone and derivatives thereof (e.g. L-menthone glycerine ketal), 2,3-dimethyl-2-(2-propyl) butanoic acid derivatives (e.g. 2,3-dimethyl-2-(2-propyl) butanoic acid-N-methylamide [WS23]), isopulegol or its esters (l-(−)-isopulegol, l-(−)-isopulegol acetate), menthane derivates (e.g. p-menthane-3,8-diol), cubebol or synthetic or natural mixtures, containing cubebol, pyrrolidone derivatives of cycloalkyldione derivatives (e.g. 3-methyl-2(1-pyrrolidinyl)-2-cyclopenten-1-one) or tetrahydropyrimidin-2-ones (e.g. icilin or related compounds, as described in WO 2004/026840), other coolants as described in W2011061330, in particular, derivatives of differently substituted cinnamic- and 2-phenoxy acids, particularly preferred methylene dioxy cinnamic acid-N,N-diphenylamide, methylene dioxy cinnamic acid-N-ethyl-N-phenylamide, methylene dioxy cinnamic acid-N-pyridyl-N-phenylamide;

e) substances having astringent effect, preferably selected from the following list: catechins, e.g. epicatechins, gallocatechins, epigallocatechins and their respective gallic acid esters, e.g. epigallocatechin gallate or epicatechin gallate, their oligomers (procyanidines, proanthocyanidins, prodelphinidines, procyanirins, thearubigenins, theogallines) as well as their C- and O-glycosides; dihydroflavonoids such as dihydromyricetin, taxifolin as well as their C- and O-glycosides, flavonols such as myricetin, quercetin as well as their C- and O-glycosides, such as quercetrin, rutin, gallic acid esters of carbohydrates such as tannin, pentagalloyl glucose or their reaction products, such as elligatannine, aluminium salts, e.g. alum, Particularly at the concentrations described herein to be used according to the invention or preferably according to the invention, compounds of formula (I) or their salts or mixtures thereof advantageously often do not have any significant other or undesired flavour effects, and thus can be used particularly well in many different types of flavours.

Flavour compositions which contain combinations of compounds of the formula (I) or their salts with one or several other trigeminally (pungent, warming, stinging, biting, scratching, cooling, numbing, tingling, astringent) effective substances, are particularly advantageous, wherein their trigeminal (primary) effect can be advantageously modulated by compounds of the formula (I) or their salts. For example, a warming, pungent or cooling effect can thereby be amplified, while an astringent effect can be mitigated.

Therefore, a flavour composition is also preferred, which additionally contains one or several substances which do not correspond to the formula (I) and have an unpleasant, in particular, bitter taste, or an astringent, bitter, dry, dusty, floury, chalky and/or metallic touch, preferably selected from the group consisting of:

f) xanthin alkaloids, xanthines (caffeine, theobromine, theophylline and methylxanthine), alkaloids (quinine, brucine, strychnine, nicotine), phenolic glycosides (e.g. salicin, arbutin), flavonoid glycosides (e.g. neohesperedin, hesperidin, naringin, quercitrin, rutin, hyperosid, quercetin 3-O-glucoside, myricetin-3-O-glycosides), chalcones or chalcone glycoside (e.g. phloridzine, phloridzinxyloside), hydrolyzable tannins (gallic or ellagic acid esters of carbohydrates, e.g. pentagalloyl glucose, tannic acids), non-hydrolyzable tannins (if applicable galloylated catechins, gallocatechins, epigallocatechins or epicatechins and their oligomers, e.g. proanthyocyanidins or procyanidins, thearubigenin), flavones (e.g. quercetin, taxifolin, myricetin), phenols such as e.g. salicin, polyphenols (e.g. gamma-oryzanol, caffeic acid or their esters (e.g. chlorogenic acid and isomers)), terpenoid bitter and tanning agents (e.g. limonoides such as imonin or nomilin from citrus fruits, lupolones and humulones from hops, iridoids, secoiridoids), absinthin from wormwood, amarogentin from gentian, metallic salts (especially potassium, magnesium and calcium salts, potassium chloride, potassium gluconate, potassium carbonate, potassium sulphate, potassium lactate, potassium glutamate, potassium succinate, potassium malate, sodium sulphate, magnesium sulphate, aluminium salts, zinc salts, tin salts, iron (II) salts, iron (III) salts, chromium (II) picolinate), active pharmaceutical ingredients (e.g. fluoroquinolone antibiotics, paracetamol, aspirin, beta-lactam antibiotics, ambroxol, propylthiouracil [PROP], guaifenesin), vitamins (e.g. vitamin H, vitamins from the B-series such as vitamin B1, B2, B6, B12, niacin, pantothenic acid), denatonium benzoate, sucralose octaacetate, iron salts, aluminium salts, zinc salts, urea, unsaturated fatty acids, especially unsaturated fatty acids in emulsions, amino acids with a bitter/astringent taste (e.g. leucine, isoleucine, valine, tryptophan, proline, histidine, tyrosine, lysine or phenylalanine) and peptides or proteins with a bitter/astringent taste (especially peptides with an amino acid from the group of leucine, isoleucine, valine, tryptophan, proline or phenylalanine at the N or C-terminus), saponins, in particular, soya saponins, isoflavonoids (in particular genistein, daidzein, genistein, daidzin, their glycosides and acylated glycosides);

g) substances with a non-unpleasant primary taste (e.g. sweet, salty, spicy, sour) and/or smell, preferably selected from the group of sweeteners or sugar substitutes, preferably potassium salts (especially potassium chloride, potassium gluconate, potassium carbonate, potassium sulphate, potassium lactate, potassium glutamate, potassium succinate, potassium malate), aspartame, acesulfame K, neotame, superaspartame, saccharin, sucralose, tagatose, monellin, stevioside, rebaudiosides, rebaudioside A, rebaudioside B, rebaudioside C, rebaudioside D, rebaudioside X, rubusoside, hernandulcin, thaumatin, miraculin, glycyrrhizin, glycyrrhetinic acid, balansin A or balansin B, or derivatives thereof, cyclamate or the pharmaceutically acceptable salts of the above-mentioned compounds.

The present invention further relates to a pharmaceutical preparation, a preparation serving nutrition, oral hygiene or pleasure, comprising (A) a novel mixture according to the invention as described above,
preferably wherein
the total quantity of compound(s) of formula (I) and/or salt(s) thereof in the preparation is in the range of 0.1-1,000 mg/kg, preferably in the range of 1-1,000 mg/kg, preferably in the range of 1 to 750 mg/kg, particularly preferably in the range of 5-500 mg/kg, based on the total weight of the preparation, or (B) a compound of the formula (I), as defined above in connection with a use according to the invention, or a physiologically acceptable salt thereof, as defined above in connection with a use according to the invention, or a mixture as defined above in connection with a use according to the invention, wherein the total quantity of compound(s) of formula (I) and/or salt(s) thereof in the preparation is in the range of 0.1-1,000 mg/kg, preferably in the range of 1-1,000 mg/kg, preferably in the range of 1 to 750 mg/kg, particularly preferably in the range of 5-500 mg/kg, based on the total weight of the preparation, or (C) a flavour composition as described above, preferably wherein the total quantity of compound(s) of formula (I) and/or salt(s) thereof in the preparation is in the range of 0.1-1,000 mg/kg, preferably in the range of 1-1,000 mg/kg, preferably in the range of 1 to 750 mg/kg, particularly preferably in the range of 5-500 mg/kg, based on the total weight of the composition A preparation according to the invention preferably also comprises one or several usual base materials, auxiliaries and additives in a quantity of 5-99.9999% w/w, preferably 10 to 80% w/w, based on the total weight of the preparation, and/or water in a quantity of up to 99.9999% w/w, preferably in a quantity of 5 to 80% w/w, based on the total weight of the preparation.

Preferred according to the invention also is a preparation as described above, wherein the total quantity of compound(s) of the formula (I) and/or salt (s) thereof in the preparation is sufficient to (a) sensorially create a warming and/or pungent effect on the tongue or in the oral cavity when the preparation is used or consumed, and/or (b) reduce or mask an unpleasant taste sensation, preferably of another substance contained in the preparation, in particular, a taste sensation selected from the group consisting of astringent, bitter, dry, dusty, floury, chalky and metallic (cf. hereto above), and/or (c) increase a pleasant taste sensation, preferably of another substance contained in the preparation, in particular, a taste sensation selected from the group consisting of warming, pungent and cooling (cf. hereto above), Preferred is also a preparation according to the invention that at least comprises one further substance for modifying, masking or reducing the unpleasant taste sensation of an unpleasant-tasting substance or mixture of substances, besides the compounds of the formula (I) or their salts (as defined above). Accordingly, a combination of at least two taste modifiers is then present.

Preparations serving nutrition or pleasure according to the invention are, e.g. bakery products (e.g. bread, dry biscuits, cakes, other pastries), sweets (e.g. chocolates, chocolate bars, other sweet bars, fruit gum, hard and soft caramels, chewing gum), alcoholic or non-alcoholic beverages (e.g. cocoa, coffee, green tea, black tea, extracts enriched with (green, black) tea, tea drinks, rooibos tea, other herbal tea, wine, wine cocktails, beer, beer cocktails, liqueurs, schnapps, brandy, fruit juices, isotonic drinks, refreshment drinks, nectars, fruit and vegetable juices, fruit or vegetable juice preparations), instant beverages (e.g. instant cocoa drinks, instant tea drinks, instant coffee drinks), meat products (e.g. ham, fresh sausage or raw sausage preparations, spiced or marinated fresh or salted meat products), eggs or egg products (dry egg, egg white, egg yolk), cereal products (e.g. breakfast cereals, cereal bars, pre-cooked readymade rice products), dairy products (e.g. full-fat or fat-reduced milk or fat-free milk drinks, rice pudding, yoghurt, kefir, fresh cheese, soft cheese, hard cheese, dried milk powder, whey, butter, buttermilk, partially or completely hydrolysed lactoprotein-containing products), products from soy protein or other soybean fractions (e.g. soy milk and products made from it, isolated or enzymatically treated beverages, drinks containing soy protein, drinks containing soybean flour, soya-lecithin-containing preparations, fermented products such as tofu or tempe or products made from them and mixtures with fruit preparations and optional flavours), fruit preparations (e.g. jams, fruit ice-cream, fruit sauces, fruit fillings), vegetable preparations (e.g. ketchup, sauces, dried vegetables, frozen vegetables, pre-cooked vegetables, boiled vegetables), snacks (e.g. baked or fried potato crisps or potato dough products, corn or peanut-based pastes), fat and oil-based products or emulsions thereof (e.g. full-fat or fat-reduced mayonnaise, remoulade, dressings), other ready-to-serve meals and soups (e.g. dry soups, instant soups, pre-cooked soups), spices, seasonings, and in particular, sprinkle seasonings, which are used, for example, in the snack sector, sweetener preparations, tablets or sachets, other preparations for sweetening or whitening beverages or other foodstuffs. The preparations according to the invention can also serve as semi-finished products for the preparation of further preparations serving nutrition or pleasure.

Pharmaceutical preparations comprise a pharmaceutical active ingredient. Advantageous pharmaceutical active ingredients are, for example, steroidal anti-inflammatory substances of the corticosteroid type, such as for example hydrocortisone, hydrocortisone derivatives, such as hydrocortisone 17-butyrate, dexamethasone, dexamethasone phosphate, methylprednisolone or cortisone. Advantageous non-steroidal pharmaceutical active ingredients are, for example, inflammatory inhibitors such as oxicams such as piroxicam ortenoxicam; salicylates such as Aspirin® (acetylsalicylic acid), disalcid, solprin or fendosal; acetic acid derivatives such as diclofenac, fenclofenac, indomethacin, sulindac, tolmetin, or clindanac; fenamates such as mefenamic, meclofenamic, flufenamic or niflumic; propionic acid derivatives such as ibuprofen, naproxen, flurbiprofen, benoxaprofen or pyrazoles, such as phenyl butazone, oxyphenyl butazone, febrazone or azapropazone.

Particularly preferred pharmaceutical preparations are non-prescription products and OTC (over-the-counter) preparations containing active pharmaceutical ingredients such as paracetamol, acetylsalicylic acid or ibuprofen, vitamins (for example vitamin H, vitamins from the B series such as vitamin B1, B2, B6, B12, niacin, panthotenic acid, preferably in the form of (effervescent) tablets or capsules), minerals (preferably in the form of (effervescent) tablets or capsules) such as iron salts, zinc salts, selenium salts, products containing active pharmaceutical ingredients or extracts of ribwort (e.g. in cough syrup) or St. John's Wort.

The preparations according to the invention, which may also contain unpleasantly tasting substances or mixtures of substances (cf. hereto above), can also be in the form of capsules, tablets (uncoated as well as coated tablets, e.g.

gastric juice-resistant coatings), dragees, granules, pellets, solid mixtures, dispersions in liquid phases, as emulsions, as powders, as solutions, as pastes or as other swallowable or chewable preparations as well as a preparation with functional ingredients, as a food supplement or as balanced diets.

Mouth-care preparations according to the invention are, in particular, oral and/or dental care products such as toothpastes, tooth gels, tooth powders, mouthwashes, chewing gums and other oral care agents.

Dental care products (as the basis for mouth-care preparations) generally comprise an abrasive system (abrasive or polishing agent), such as e.g. crystalline silicas, calcium carbonates, calcium phosphates, aluminium oxides and/or hydroxylapatites, surfactants, e.g. sodium lauryl sulphate, sodium lauryl sarcosinate and/or cocamidopropyl betaine, humectants such as e.g. glycerin and/or sorbitol, thickeners such as e.g. carboxymethyl cellulose, polyethylene glycols, carrageenan and/or Laponite®, sweeteners such as e.g. saccharin, other taste modifiers of unpleasant taste sensations, taste modifiers of other, generally not unpleasant taste sensations, taste modifiers (e.g. inositol phosphate, nucleotides such as guanosine monophosphate, adenosine monophosphate or other substances such as sodium glutamate or 2-phenoxy propionic acid), cooling active ingredients such as e.g. menthol, menthol derivatives (e.g. L-menthol, L-menthyl lactate, L-menthylalkyl carbonate, menthone ketals, menthane carboxamides), 2,2,2-trialkyl aceteamides (e.g. 2,2-diisopropyl propionic acid methylamide), methylene dioxy cinnamic acid-N, N-diphenylamide, methylene dioxy cinnamic acid-N-ethyl-N-phenylamide, methylene dioxy cinnamic acid-N-pyridyl-N-phenylamide, icilin derivatives, stabilisers and active ingredients, such as sodium fluoride, sodium monofluorophosphate, tin difluoride, quaternary ammonium fluorides, zinc citrate, zinc sulphate, tin pyrophosphate, tin dichloride, mixtures of various pyrophosphates, triclosan, cetyl pyridinium chloride, aluminium lactate, potassium citrate, potassium nitrate, potassium chloride, strontium chloride, hydrogen peroxide, flavours and/or sodium bicarbonate or odour modifiers.

Chewing gums (as a further example of mouth-care preparations) generally comprise a chewing gum base, i.e. a chewing mass that plasticises during chewing, sugars of various types, sugar substitutes, sweeteners, sugar alcohols, other taste modifiers for unpleasant tastes, taste modifiers for other, generally not unpleasant tastes, taste modifiers (e.g. inositol phosphate, nucleotides such as guanosine monophosphate, adenosine monophosphate, or other substances such as sodium glutamate or 2-phenoxy propionic acid), the cooling active ingredients, humectants, thickeners, emulsifiers, flavours and stabilisers or odour modifiers mentioned in the previous section.

Examples of usual base materials, auxiliaries and additives for preparations according to the invention are water, mixtures of fresh or processed, plant or animal base or raw materials (e.g. raw, fried, dried, fermented, smoked and/or cooked meat, bone, cartilage, fish, vegetables, fruits, herbs, nuts, vegetable or fruit juices or pastes or mixtures thereof), digestible or indigestible carbohydrates (e.g. sucrose, maltose, fructose, glucose, dextrins, amylose, amylopectin, inulin, xylans, cellulose), sugar alcohols (e.g. sorbitol), natural or hardened fats (e.g. tallow, lard, palm fat, coconut fat, hydrogenated vegetable fat), oils (e.g. sunflower oil, peanut oil, corn oil, olive oil, fish oil, soybean oil, sesame oil), fatty acids or salts thereof (e.g. potassium stearate), proteinogenic or non-proteinogenic amino acids and related compounds (e.g. taurins), peptides, native or processed proteins (e.g. gelatin), enzymes (e.g. peptidases), nucleic acids, nucleotides, taste modifiers other than those used according to the invention for unpleasant taste sensations (e.g. hesperetin, phloretin or other hydroxychalcone derivatives to be used according to US 2008/0227867, as well as the lactones described therin, if applicable), taste modifiers for other, generally not unpleasant taste sensations, taste modifiers (e.g. inositol phosphate, nucleotides such as guanosine monophosphate, adenosine monophosphate or other substances such as sodium glutamate or 2-phenoxy propionic acid), emulsifiers (e.g. lecithins, diacylglycerols), stabilisers (e.g. carrageenan, alginate), preservatives (e.g. benzoic acid, sorbic acid), antioxidants (e.g. tocopherol, ascorbic acid), chelators (e.g. citric acid), organic or inorganic acidifiers (e.g. malic acid, acetic acid, citric acid, tartaric acid, phosphoric acid, lactic acid), bitter additives (e.g. quinol, caffeine, limonin, aminogentin, humolones, lupolones, catechins, tannins), sweeteners (e.g. saccharin, cyclamate, aspartame, neotame, stevioside, rebaudioside, acesulfame K, neohesperidine dihydrochalcone, thaumatin, superaspartame), mineral salts (e.g. sodium chloride, potassium chloride, magnesium chloride, sodium phosphates), anti-enzymatic-browning agents (e.g. sulphites, ascorbic acid), essential oils, plant extracts, natural or synthetic dyes or colour pigments (e.g. carotenoids, flavonoids, anthocyanins, chlorophyll and derivatives thereof), spices, synthetic, natural or nature-identical flavours or fragrances as well as odour modifiers.

The present invention also relates to a method for producing a pharmaceutical preparation, a preparation serving nutrition, oral hygiene or pleasure, preferably a preparation according to the invention, in particular, one as described herein as being preferred, comprising the following steps:

i) Providing
(A) a mixture according to the invention as described herein,
preferably wherein
the total quantity of compound(s) of formula (I) and/or salt(s) thereof is selected such that the total quantity in the preparation to be made is in the range of 0.1-1,000 mg/kg, preferably in the range of 1-1,000 mg/kg, preferably in the range of 1 to 750 mg/kg, particularly preferably in the range of 5-500 mg/kg, based on the total weight of the preparation,
or
(B) a compound of the formula (I) as defined herein according to the invention or to be used according to the invention, or a physiologically acceptable salt thereof as defined herein or a mixture as defined herein,
wherein
the total quantity of compound(s) of formula (I) and/or salt(s) thereof is selected such that the total quantity in the preparation to be made is in the range of 0.1-1,000 mg/kg, preferably in the range of 1-1,000 mg/kg, preferably in the range of 1 to 750 mg/kg, particularly preferably in the range of 5-500 mg/kg, based on the total weight of the preparation,
or
(C) a flavour composition according to the invention as described herein,
preferably wherein
the total quantity of compound(s) of formula (I) and/or salt(s) is selected such that the total quantity in the preparation to be made is in the range of 0.1-1,000 mg/kg, preferably in the range of 1-1, 000 mg/kg, preferably in the range of 1 to 750 mg/kg, particularly preferably in the range of 5-500 mg/kg, based on the total weight of the preparation,
ii) providing one or several further components of the preparation to be made, and
iii) contacting or mixing the further components provided in step ii) with the component(s) provided in step i), preferably in a sensorially effective quantity.

The described preparations according to the invention are preferably prepared by incorporating an ester of homovanillic acid to be used according to the invention, as a substance, as a solution or in the form of a flavour composition into a pharmaceutical base preparation serving nutrition, oral care or pleasure. Advantageously, preparations according to the invention being present as liquids can also be converted into a solid preparation, e.g. by spray drying.

Below, the production of flavour compositions according to the invention (here: containing ethyl homovanillate (17) is described by way of example by reacting
i) 1 equivalent ascorbic acid or one of its physiologically acceptable salts with
ii) 1 equivalent vanillyl alcohol
iii) in a (50/50; v/v) mixture of water and a representative from the group of substance of alcohols, particularly preferred are ethanol, propanol, butanol, pentanol, hexanol and isopropyl alcohol
iv) at a temperature of 100-150° C. (under pressure, if applicable)
v) for a time period of 4-6 h.

This flavour preparation (primary reaction mixture) preferably contains 1,000-200,000 ppm, preferably 10,000-100,000 ppm ethyl homovanillate (17) and can be used as such or, if appropriate, further purified in admixture with other flavourings and carriers as a flavour composition. These flavour compositions preferably contain 100-100,000 mg/kg, preferably 250-40,000 mg/kg, particularly preferably 250-15,000 mg/kg ethyl homovanillate (17) or physiologically acceptable salts, in particular, its sodium, potassium, ammonium, calcium, magnesium or zinc salts, wherein the concentration of ethyl homovanillate (17) or mixtures of ethyl homovanillate (17) with the corresponding salts in the final food products preferably corresponds to 0.1-1,000 mg/kg, preferably 1-750 mg/kg, particularly preferably 5-500 mg/kg.

Ascorbic acid and vanillyl alcohol are each found in nature in foodstuffs and are permitted as food additives or flavourings; therefore, the use of isolated or naturally obtained ascorbic acid, as well as of isolated or naturally obtained vanillyl alcohol, which can also be used in the form of incompletely purified extracts or fractions is particularly advantageous. Vanillyl alcohol is present, e.g. in beer (Flavor-Base, 9th Edition, Leffingwell & Associates, 2013) or the Sitka spruce (*Picea sitchensis*, P. J. Kohlbrenner, C. Schuerch, Benzene-Alcohol-Soluble Extractives of Sitka Spruce, *J. Org. Chem.* 1959, 24(2), 166-172).

The above-described flavour preparations according to the invention are characterised by the fact that they can contain, in addition to ethyl homovanillate (17), at least one further substance from the following Table 1 (The same applies accordingly to the flavour preparations according to the invention described herein):

TABLE 1

| No. | Retention time [min]* | Molar mass m/z (Found: ESI+) | IPUAC name | Structure |
|---|---|---|---|---|
| 1* | 2.88 | found 227.0546 calc. 226.047189 for $C_{10}H_{10}O_6$ | 3-(1,2-dihydroxyethyl)-1,3-dihydroisobenzofuran-1,4,5-triol | 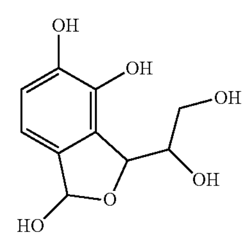 [SMILES: OCC(O)C1OC(O)c2ccc(O)c(O)c21] |
| 2 | 3.73 | found 313.0921 calc. 312.083969 for $C_{14}H_{16}O_8$ | 6-[(3-hydroperoxy-4-hydroxyphenyl)-methyl]-3,6,6a-trihydroxy-3,3a-dihydro-2H-furo[3,2-b]furan-5-one* | 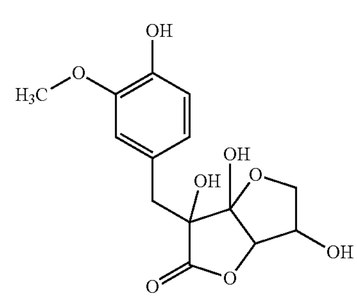 [SMILES: COc1cc(CC2(O)C(=O)OC3C(O)COC32O)ccc1O] |

TABLE 1-continued

| No. | Retention time [min]* | Molar mass m/z (Found: ESI+) | IPUAC name | Structure |
|---|---|---|---|---|
| 3 | 3.98 | found 313.0920<br>calc. 312.083969<br>for $C_{14}H_{16}O_8$ | 2-hydroxy-3-(4-hydroxy-3-methoxyphenyl)-2-(3-hydroxy-2-oxo-tetrahydrofuran-3-yl) propanoic acid | 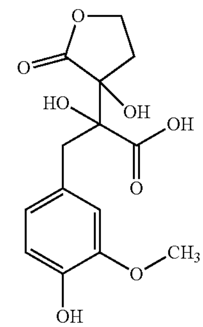 [SMILES: COc1cc(CC(O)(C(=O)O)C2(O)CCOC2=O)ccc1O] |
| 4 | 4.66 | found 251.0924<br>calc. 250.083575<br>for $C_{13}H_{14}O_5$ | 2-hydroxy-3-(4-hydroxy-3-methoxyphenyl)-4-(hydroxymethyl) cyclopent-2-en-1-one* | 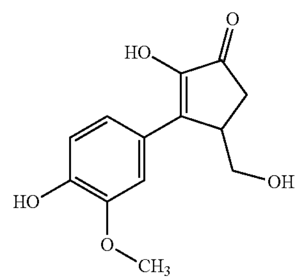 [SMILES: COc1cc(C2=C(O)C(=O)CC2CO)ccc1O] |
| 5 | 6.12 | found 387.1449<br>calc. 386.136004<br>for $C_{21}H_{22}O_7$ | 2-hydroxy-3-[4-hydroxy-2-[(4-hydroxy-3-methoxyphenyl) methyl]-5-methoxyphenyl]-4-(hydroxymethyl) cyclopent-2-en-1-one | 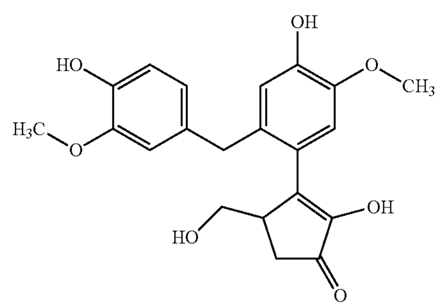 |
| 6 | 6.33 | found 251.0925<br>calc. 250.083575<br>for $C_{13}H_{14}O_5$ | 2-[(4-hydroxy-3-methoxyphenyl)-methylene]-5-(hydroxymethyl) tetrahydrofuran-3-one | 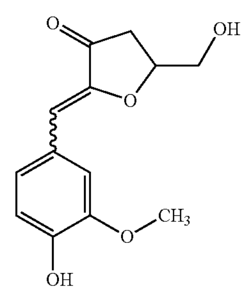 [SMILES: COc1cc(C=C2OC(CO)CC2=O)ccc1O] |
| 7 | 6.34 | found 251.0921<br>calc. 250.083575<br>for $C_{13}H_{14}O_5$ | 5-hydroxy-6-[(4-hydroxy-3-methoxyphenyl) methyl]-2,3-dihydropyran-4-one | 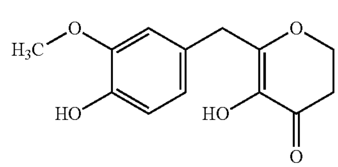 [SMILES: COc1cc(CC2=C(O)C(=O)CCO2)ccc1O] |

TABLE 1-continued

| No. | Retention time [min]* | Molar mass m/z (Found: ESI+) | IPUAC name | Structure |
|---|---|---|---|---|
| 8 | 6.98 | found 341.1251<br>calc. 340.115269<br>for $C_{16}H_{20}O_8$ | Ethyl-2-hydroxy-3-(4-hydroxy-3-methoxyphenyl)-2-(3-hydroxy-2-oxo-tetrahydro-furan-3-yl)propanoate | 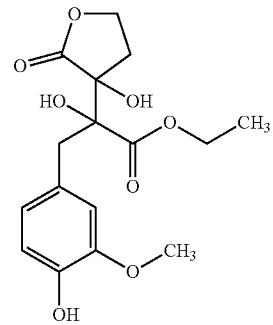 [SMILES: CCOC(=O)C(O)(Cc1ccc(O)c(OC)c1)C1(O)CCOC1=O] |
| 9 | 7.68 | found 233.0842<br>calc. 232.073010<br>for $C_{13}H_{12}O_4$ | 1-(2-furyl)-2-(4-hydroxy-3-methoxyphenyl) ethanone | 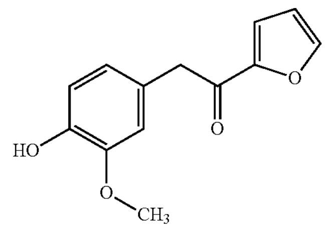 [SMILES: COc1cc(CC(=O)c2ccco2)ccc1O] |
| 10 | 7.71 | found 387.1457<br>calc. 386.136004<br>for $C_{21}H_{22}O_7$ | 2-hydroxy-3-[4-hydroxy-3-[(4-hydroxy-3-methoxyphenyl) methyl]-5-methoxyphenyl]-4-(hydroxymethyl) cyclopent-2-en-1-one | 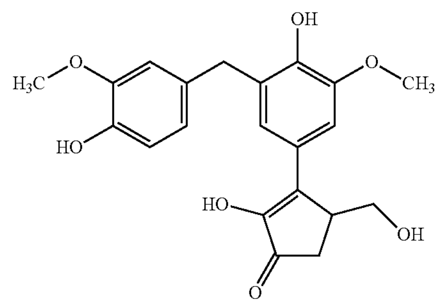 |
| 11 | 7.93 | found 233.0821<br>calc. 233.073010<br>for $C_{13}H_{12}O_4$ | 2-[(4-hydroxy-3-methoxyphenyl) methylene]-5-methyl furan-3-one | 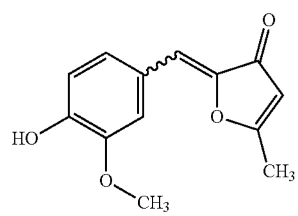 [SMILES: COc1cc(C=C2OC(C)=CC2=O)ccc1O] |
| 12 | 8.22 | found 297.1347<br>calc. 296.125440<br>for $C_{15}H_{20}O_6$ | Ethyl-3-[3-(4-hydroxy-3-methoxyphenyl)-2-oxo-propoxy] propanoate | 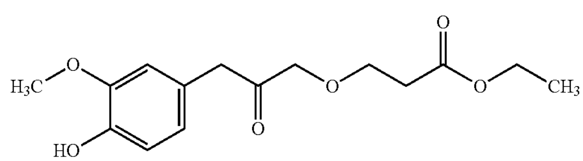 [SMILES: CCOC(=O)CCOCC(=O)Cc1ccc(O)c(OC)c1] |
| 14 | 8.82 | found 465.1606<br>calc. 464.146569<br>for $C_{26}H_{24}O_8$ | 2-[3-(2-furyl)-1,2-bis(4-hydroxy-3-methoxyphenyl)-3-oxo-propyl]-5-methyl furan-3-one | 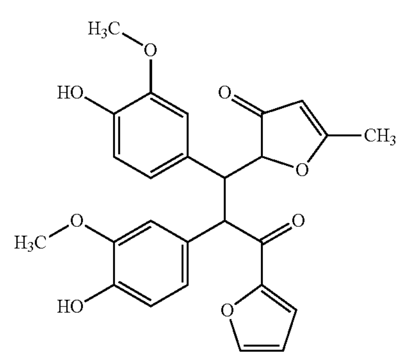 |

TABLE 1-continued

| No. | Retention time [min]* | Molar mass m/z (Found: ESI+) | IPUAC name | Structure |
|---|---|---|---|---|
| 15 | 9.52 | found 369.1346 calc. 368.125440 for $C_{21}H_{20}O_6$ | 1-(2-furyl)-2-[4-hydroxy-2-[(4-hydroxy-3-methoxyphenyl)methyl]-5-methoxy-phenyl]ethanone | 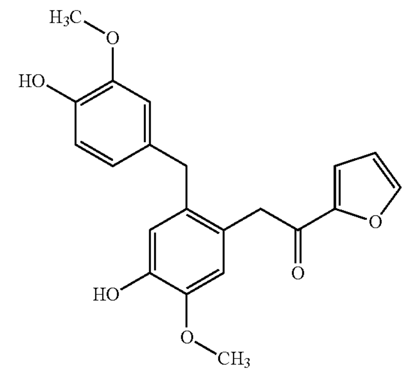 [SMILES: COc1cc(Cc2cc(O)c(OC)cc2CC(=O)c2ccco2)ccc1O] |

*cf. Preobrazhenskaya, M.N. et al. *Tetrahedron* 1997, 53, 6971-6976

The primary reaction mixture can be purified by one or several of the following methods:

a) If applicable, concentrating the primary reaction mixture, preferably by one or several evaporative or pervaporative processes,
b) If applicable, treating the primary reaction mixture (optionally concentrated in step a), if applicable) by partition chromatographic (e.g. countercurrent distribution processes such as FCPC, SCCC, Craig process) or adsorption chromatographic processes with or at adsorbents, preferably selected from the group consisting of silica gel, modified silica gel, activated carbon, zeolite, bentonite, diatomaceous earth, alumina, basic or acidic or neutral, optionally macroporous, ion exchanger, preferably by batch or column process, with the aid of further extracting agents, if applicable, whereby a purified flavour composition is obtained,
c) If applicable, drying the purified flavour composition obtained in step b), preferably by an evaporative or pervaporative process,
d) If applicable, repeating the steps b) and c) once or several times
e) If applicable, mixing the purified flavour composition obtained in the preceding steps with a suitable diluent or a mixture of two or several diluents, preferably selected from the group consisting of ethanol, isopropanol, 1,2-propylene glycol, vegetable oil triglycerides, diacetin, triacetin and glycerin, wherein preferably the flavour composition is obtained in the form of a solution.

According to a another preferred embodiment, compounds of formula (I) or their salts or an aroma composition according to the invention in particular, the primary reaction mixture (as described above by way of example) or the purified flavour composition (as described above by way of example) and other components of the preparation according to the invention in the form of emulsions, in liposomes, e.g. starting from phosphatidyl choline, in microspheres, in nanospheres, or also in capsules, granules or extrudates from a matrix suitable for standard and luxury food, e.g. from starch, starch derivatives, cellulose or cellulose derivatives (e.g. hydroxypropyl cellulose), other polysaccharides (e.g. alginate), natural fats, natural waxes (e.g. beeswax, carnauba wax), or from proteins, e.g. gelatin, to be used according to the invention are incorporated for producing preparations according to the invention. In a preferred preparation process, the compounds of formula (I) or their salts are complexed with one or several suitable complexing agents, for example with cycloglycans, e.g. cyclofructans, cyclodextrins or cyclodextrin derivatives, preferably alpha, beta and gamma cyclodextrin, and are used in this complexed form.

The present invention is further described below by means of selected, specific examples. The examples only serve the purpose of illustrating the invention, without any limitation. Unless specified otherwise, all details provided relate to the weight.

EXAMPLES

Example 1: Production of a Flavour Preparation (Primary Reaction Mixture) Containing Ethyl Homovanillate (17) by Reaction of Ascorbic Acid with Vanillyl Alcohol 3 mmol ascorbic acid and 3 mmol vanillyl alcohol were dissolved in 10 ml water/ethanol (1/1; v/v). The solution was heated to 100° C. with constant stirring in the microwave (Mars Synthesis, CEM) for 7 minutes. The reaction mixture was subsequently heated in the microwave with constant stirring for further 6 h at 100° C. The LC-MS/QTOF chromatogram illustrated below shows the substances that are listed in Table 1 and form after 6 h as well as ethyl homovanillate (EHV, 17). Ethyl homovanillate (17) is contained in the primary reaction mixture at a quantity of 1.2%.

Carrying out the above reaction with the indicated ratios of ascorbic acid and vanillyl alcohol with a boiling time of 4 h also leads to the formation of EHV.

In this regard, refer to FIG. 1 (LC-MS/QTOF chromatogram of the primary reaction mixture after 6 h at 100° C.; upper chromatogram mass trace ESI positive, lower chromatogram UV-VIS totalled; the numbers represent the compounds according to Table 1 and EHV stands for ethyl homovanillate (17)).

Example 2: Isolation of Ethyl Homovanillate (17) from a Flavour Preparation (Primary Reaction Mixture)

The primary reaction mixture is pre-fractionated using medium-pressure liquid chromatography (MPLC) (column material: Lewatit VP OC 1064; water/ethanol 3/1; v/v).

Subsequently, further separation is carried out via preparative high-pressure liquid chromatography (pHPLC) (column: Phenomenex Luna C18 5μ 150×21.2 mm, flow rate 30 ml/min, detection 210 nm) in the isocratic mode (63% H₂O, 37% MeOH). Final isolation of ethyl homovanillate (17) is carried out via semi-preparative high-pressure liquid chromatography (sPHPLC) in the gradient mode (column: YMC Triart C18 5μ 250×10 mm; A: H₂O; B: MeOH; 0 min 65% A, 35% B; 25 min 40% A, 60% B; 30 min 100% B; flow rate 3 ml/min; detection: 250 nm). The obtained ethyl homovanillate (17) was subsequently freeze-dried and tasted and sensorially assessed at a dosage of 100 ppm in 5% sugar solution, 0.5% salt solution, 500 ppm caffeine solution and water.

| Medium | Taste description |
| --- | --- |
| Water | Pungent, stinging, slightly warming |
| 5% sugar solution | Pungent, warming |
| 0.5% salt solution | Pungent |

Example 3: Preparation and Sensorial Assessment of a Fraction (Purified Flavour Preparation) Containing Ethyl Homovanillate (17)

The primary reaction mixture is divided into 12 fractions using LC-Taste® (according to WO 2006 111,476) in the gradient mode (Hamilton PRP-1 10μ 250×21.5 mm; A: H₂O, B: EtOH; 0 min 100% A; 25 min 75% A, 25% B; 40 min 100% B; flow rate: 10 ml/min, oven temperature: 80° C.), wherein the fractions were divided based on the UV trace at 210 nm. Following the narrowing of the fractions to 0.5 ml on the Büchi Syncore at 40° C., the residue was dissolved in 10 ml water. 2 ml of each one of these solutions was mixed mit 18 ml 3.33% sugar solution (corresponds to a final dose of 96 mg/kg ethyl homovanillate (17) for fraction 10 and 26 mg/kg ethyl homovanillate for fraction 11 in 3% sugar solution) and subjected to sensorial assessment.

Figure 2:
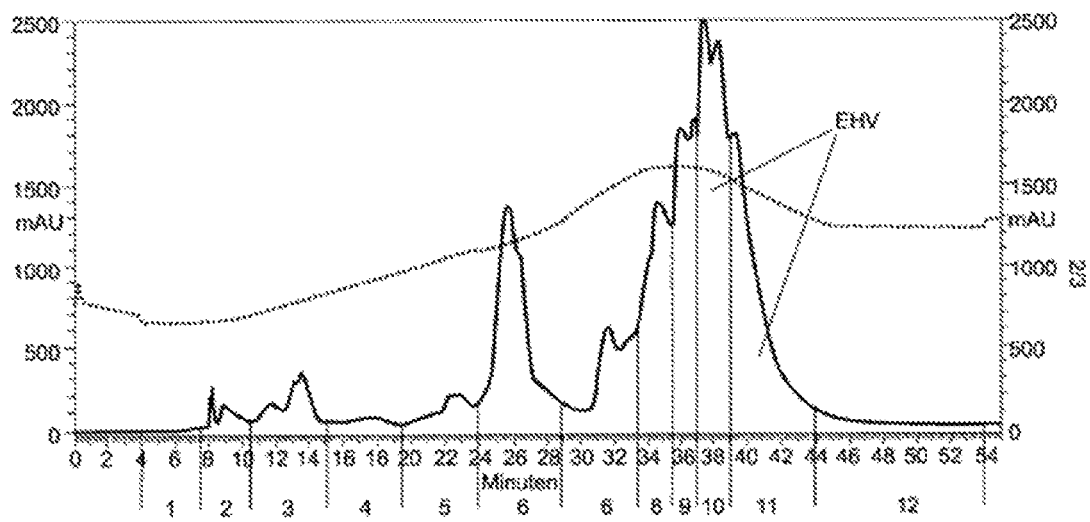
FIG. 2 is a chromatogram graph of the primary reaction mixture divided into 12 fractions based on the UV trace at 210 nm using LC-Taste® in accordance with aspects of the invention.

To this end, see FIG. 2 (LC Taste Chromatogram of the primary reaction mixture; Fraction 10 and 11 contain EHV)

TABLE 2

Sensory taste profile of the fractions 10 and 11 of LC taste separation (see FIG. 2)

| Fraction | Taste | Intensity |
| --- | --- | --- |
| 10 | Warming | 5-6 |
|  | Medical | 4-5 |
|  | Pepper | 3-4 |
|  | Smoked ham (smoky) | 3 |
|  | Pungent | 5 |
| 11 | Warming | 2-3 |
|  | Smoked ham | 4-5 |
|  | Smoky | 4 |
|  | Grilled, BBQ | 4 |
|  | Phenolic | 3 |
|  | Vanilla | 2 |

Example 4: Synthesis of Homovanillinic Acid Esters

Method A:

Homovanillic acid (1.5-3 g) was provided with the respective alcohol (equimolar) in toluene (100 ml), conc. sulphuric acid was added to it and heated to the boiling point at the water separator for 5 h. It was washed once with saturated aqueous NaHCO₃ solution, twice with water or alternately with saturated aqueous NaCl solution and the solvent was removed under vacuum. The product was obtained by column chromatography on silica gel with a yield of about 70%.

Method B:

Homovanillinic acid (1.5-3 g) was stirred with the respective alcohol (100 ml) and 0.2-0.5 equivalent of sulphuric acid for 7 h at 90° C. (heating block temperature). Majority of the alcohol was removed under vacuum, saturated aqueous NaHCO₃ solution and EtOAc were added, the organic phase separated and the aqueous phase extracted once with EtOAc. The combined organic phases were washed once with saturated aqueous NaHCO₃ solution and with water or alternately with saturated aqueous NaCl solution, dried over NaSO₄ and the solvent was removed under vacuum. The product was obtained by column chromatography on silica gel with a 90% to quantitative yield.

Isopropyl-2-(4-hydroxy-3-methoxyphenyl) acetate (7, method B)

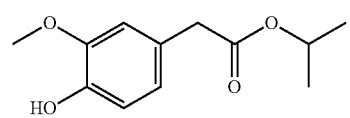

7

¹H-NMR (400 MHz, CDCl₃): δ=6.85 (d, J=8.1 Hz, 1H), 6.81 (dd, J=2.0, 0.5 Hz, 1H), 6.76 (ddt, J=8.0, 2.0, 0.6 Hz, 1H), 5.60 (s, 1H), 5.01 (hept, J=6.3 Hz, 1H), 3.88 (s, 3H), 3.496 (t, J=0.5 Hz, 2H), 1.23 (d, J=6.3 Hz, 6H).

¹³C-NMR (100 MHz, CDCl₃): δ=171.5, 146.4, 144.7, 126.1, 122.1, 114.3, 111.7, 68.1, 55.9, 41.3, 21.8 (2C).

GCMS: m/z (%)=224 [M⁺] (30), 137 (100), 122 (10), 107 (2), 94 (6), 77 (3), 66 (5), 51 (3), 43 (15).

sec-Butyl-2-(4-hydroxy-3-methoxyphenyl) acetate (8, method B)

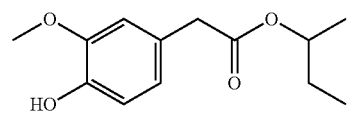

8

¹H-NMR (400 MHz, CDCl₃): δ=6.85 (d, J=8.1 Hz, 1H), 6.82 (d, J=1.9 Hz, 1H), 6.79-6.74 (m, 1H), 5.57 (s, 1H), 4.92-4.78 (m, 1H), 3.88 (s, 3H), 3.51 (t, J=0.5 Hz, 2H), 1.62-1.46 (m, 2H), 1.19 (d, J=6.3 Hz, 3H), 0.85 (t, J=7.5 Hz, 3H).

¹³C-NMR (100 MHz, CDCl₃): δ=171.6, 146.4, 144.7, 126.2, 122.1, 114.3, 111.7, 72.7, 55.9, 41.4, 28.8, 19.4, 9.6.

GCMS: m/z (%)=238 [M⁺] (30), 137 (100), 122 (8), 107 (2), 94 (5), 77 (2), 66 (3), 57 (20), 51 (2), 41 (8), 29 (8).

Isobutyl-2-(4-hydroxy-3-methoxyphenyl) acetate (9, method B)

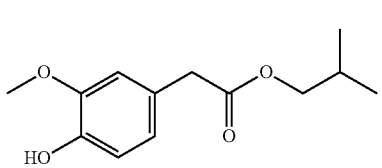

¹H-NMR (400 MHz, CDCl₃): δ=6.85 (dd, J=8.1, 0.3 Hz, 1H), 6.82-6.81 (m, 1H), 6.77 (ddt, J=8.1, 2.0, 0.6 Hz, 1H), 5.60 (s, 1H), 3.87 (d, J=0.3 Hz, 3H), 3.86 (d, J=6.6 Hz, 2H), 3.54 (t, J=0.5 Hz, 2H), 1.91 (dq, J=6.7 Hz, 1H), 0.90 (d, J=6.7 Hz, 6H).

¹³C-NMR (100 MHz, CDCl₃): δ=172.0, 146.5, 144.7, 126.0, 122.1, 114.3, 111.7, 70.9, 55.9, 41.1, 27.7, 19.0 (2C).

GCMS: m/z (%)=238 [M⁺] (30), 182 (5), 137 (100), 122 (9), 107 (2), 94 (6), 77 (2), 66 (3), 57 (11), 51 (2), 41 (8), 29 (7).

Butyl-2-(4-hydroxy-3-methoxyphenyl) acetate (19, method B)

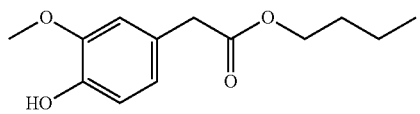

¹H-NMR (400 MHz, CDCl₃): δ=6.85 (d, J=8.1 Hz, 1H), 6.81 (dd, J=2.0, 0.5 Hz, 1H), 6.76 (ddt, J=8.1, 1.9, 0.6 Hz, 1H), 5.60 (s, 1H), 4.09 (t, J=6.7 Hz, 2H), 3.87 (d, J=0.3 Hz, 3H), 3.53 (t, J=0.5 Hz, 2H), 1.67-1.55 (m, 2H), 1.42-1.29 (m, 2H), 0.91 (t, J=7.4 Hz, 3H).

¹³C-NMR (100 MHz, CDCl₃): δ=172.0, 146.5, 144.7, 126.0, 122.1, 114.3, 111.7, 64.7, 55.9, 41.1, 30.6, 19.1, 13.7.

GCMS: m/z (%)=238 [M⁺] (27), 182 (2), 137 (100), 122 (9), 107 (2), 94 (5), 77 (2), 66 (2), 57 (4), 41 (5), 29 (8).

Propyl-2-(4-hydroxy-3-methoxyphenyl) acetate (18, method B)

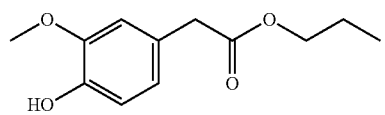

¹H-NMR (400 MHz, CDCl₃): δ=6.85 (d, J=8.0 Hz, 1H), 6.81 (d, J=2.0 Hz, 1H), 6.76 (dd, J=8.1, 2.0 Hz, 1H), 5.61-5.58 (m, 1H), 4.05 (t, J=6.7 Hz, 2H), 3.88 (s, 3H), 3.54 (s, 2H), 1.71-1.52 (m, 2H), 0.91 (t, J=7.4 Hz, 3H).

¹³C-NMR (100 MHz, CDCl₃): δ=172.0, 146.5, 144.7, 126.0, 122.2, 144.3, 111.7, 66.4, 55.9, 41.1, 22.0, 10.4.

GCMS: m/z (%)=224 [M⁺] (30), 137 (100), 122 (10), 107 (2), 94 (8), 77 (2), 66 (3), 51 (2) 43 (8).

Ethyl-2-(4-hydroxy-3-methoxyphenyl) acetate (17, method B)

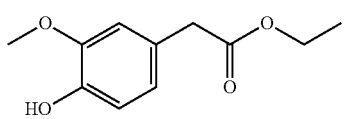

¹H-NMR (400 MHz, CDCl₃): δ=6.85 (d, J=8.05 Hz, 1H), 6.81 (d, J=1.94 Hz, 1H), 6.76 (ddd, J=8.01, 1.99, 0.50 Hz, 1H), 5.61 (d, J=0.36 Hz, 1H), 4.15 (q, J=7.13 Hz, 2H), 3.88 (s, 3H), 3.53 (d, J=0.57 Hz, 2H), 1.25 (t, J=7.13 Hz, 1H).

¹³C-NMR (100 MHz, CDCl₃): δ=172.0, 146.5, 144.7, 125.9, 122.1, 114.4, 111.7, 60.8, 55.9, 41.0, 14.2.

GCMS: m/z (%)=210 [M⁺] (30), 137 (100), 122 (11), 107 (2), 94 (8), 77 (2), 66 (3), 51 (3), 39 (3), 29 (8).

Hexyl-2-(4-hydroxy-3-methoxyphenyl) acetate (21, method A)

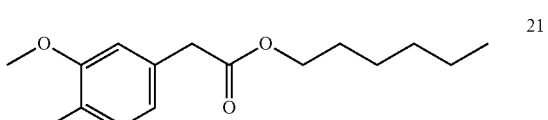

¹H-NMR (400 MHz, CDCl₃): δ=6.85 (dd, J=8.1, 0.3 Hz, 1H), 6.81 (d, J=2.0 Hz, 1H), 6.76 (ddq, J=8.1, 2.0, 0.5 Hz, 1H), 5.58 (s, 1H), 4.08 (t, J=6.7 Hz, 2H), 3.88 (s, 3H), 3.53 (s, 2H), 1.65-1.56 (m, 2H), 1.36-1.20 (m, 6H), 0.87 (t, J=7.0 Hz, 3H).

¹³C-NMR (100 MHz, CDCl₃): δ=172.0, 146.5, 144.7, 126.0, 122.1, 114.3, 111.7, 65.0, 55.9, 41.1, 31.4, 28.6, 25.5, 22.5, 14.0.

GCMS: m/z (%)=266 [M⁺] (30), 182 (8), 137 (100), 122 (8), 107 (2), 94 (4), 77 (2), 66 (2), 55 (3), 43 (13).

3-Phenylpropyl-2-(4-hydroxy-3-methoxyphenyl) acetate (22, method A)

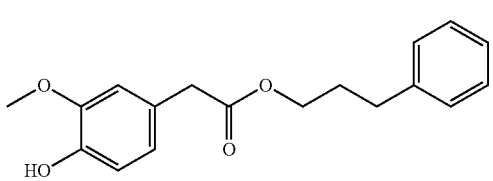

¹H NMR (600 MHz, CDCl₃): δ=7.29-7.24 (m, 2H), 7.20-7.16 (m, 1H), 7.14-7.10 (m, 2H), 6.87 (d, J=8.0 Hz, 1H), 6.81 (d, J=2.0 Hz, 1H), 6.78 (dd, J=8.1, 2.0 Hz, 1H), 5.57 (s, 1H), 4.10 (t, J=6.5 Hz, 2H), 3.88 (s, 3H), 3.54 (s, 2H), 2.64 (dd, J=8.5, 6.8 Hz, 2H), 1.98-1.90 (m, 2H).

¹³C NMR (151 MHz, CDCl₃): δ=171.91, 146.46, 144.75, 141.09, 128.42, 128.37, 126.00, 125.88, 122.13, 114.36, 111.68, 64.10, 55.90, 41.08, 32.06, 30.16.

GCMS: m/z (%)=300 [M+] (28), 182 (62), 137 (100), 122 (16), 118 (20), 91 (34), 77 (6), 65 (6), 51 (4), 28(4).

4-Phenylbutyl-2-(4-hydroxy-3-methoxyphenyl) acetate (23, method A)

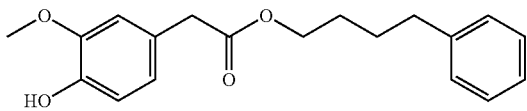

¹H NMR (600 MHz, CDCl₃): δ=7.29-7.25 (m, 2H), 7.20-7.16 (m, 1H), 7.15-7.11 (m, 2H), 6.85 (d, J=8.1 Hz, 1H), 6.79 (d, J=2.0 Hz, 1H), 6.75 (dd, J=8.0, 2.0 Hz, 1H), 5.60 (s, 1H), 4.10 (t, J=6.1 Hz, 2H), 3.83 (s, 3H), 3.52 (s, 2H), 2.60 (t, J=7.1 Hz, 2H), 1.69-1.60 (m, 4H).
¹³C NMR (151 MHz, CDCl₃): δ=171.97, 146.45, 144.72, 141.97, 128.33, 128.32, 125.86, 125.81, 122.09, 114.35, 111.67, 64.67, 55.84, 41.06, 35.38, 28.17, 27.68.
GCMS: m/z (%)=314 [M+] (48), 182 (36), 137 (100), 122 (10), 104 (20), 91 (44), 65 (4), 51 (2).

[(Z)-Hex-3-enyl]-2-(4-hydroxy-3-methoxyphenyl) acetate (6, method A)

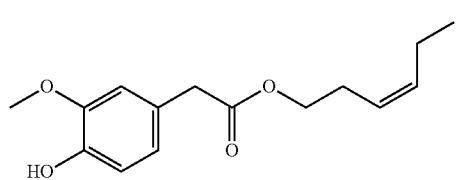

¹H-NMR (400 MHz, CDCl₃): δ=6.85 (d, J=8.1 Hz, 1H), 6.80 (d, J=2.0 Hz, 1H), 6.76 (dd, J=8.0, 2.0 Hz, 1H), 5.58 (s, 1H), 5.49 (ddt, J=10.9, 7.3, 1.6 Hz, 1H), 5.29 (ddt, J=10.7, 7.3, 1.5 Hz, 1H), 4.08 (t, J=7.0 Hz, 2H), 3.88 (s, 3H), 3.53 (s, 2H), 2.43-2.32 (m, 2H), 2.03 (pd, J=7.5, 1.6 Hz, 2H), 0.96 (t, J=7.5 Hz, 3H).
¹³C-NMR (100 MHz, CDCl₃): δ=171.9, 146.5, 144.7, 134.6, 125.8, 123.6, 122.1, 114.3, 111.7, 64.4, 55.9, 41.0, 26.7, 20.6, 14.2.
GCMS: m/z (%)=264 [M+] (30), 182 (55), 137 (100), 122 (15), 94 (10), 82 (8), 67 (15), 55 (20), 41 (15).

2-Methylbutyl-2-(4-hydroxy-3-methoxyphenyl) acetate (12, method B)

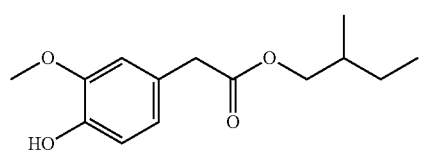

¹H-NMR (400 MHz, CDCl₃): δ=6.86 (d, J=8.1 Hz, 1H), 6.81 (d, J=2.0 Hz, 1H), 6.77 (dd, J=8.0, 2.0 Hz, 1H), 5.55 (s, 1H), 3.97 (dd, J=10.7, 6.0 Hz, 1H), 3.90 (dd, J=10.8, 6.7 Hz, 1H), 3.88 (s, 3H), 3.54 (s, 2H), 1.69 (dddd, J=12.4, 7.8, 6.8, 5.8 Hz, 1H), 1.38 (dtd, J=13.1, 7.5, 5.6 Hz, 1H), 1.23-1.08 (m, 1H), 0.88 (d, J=6.8 Hz, 3H), 0.88 (t, J=7.5 Hz, 3H).

¹³C-NMR (100 MHz, CDCl₃): δ=172.0, 146.4, 144.7, 126.0, 122.1, 114.3, 111.7, 69.4, 55.9, 41.1, 34.1, 26.0, 16.3, 11.2.
GCMS: m/z (%)=252 [M+] (30), 182 (10), 137 (100), 122 (8), 94 (7), 71 (5), 55 (4), 43 (18), 29 (10).

2-Phenylethyl-2-(4-hydroxy-3-methoxyphenyl) acetate (1, method A)

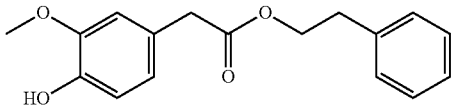

¹H-NMR (400 MHz, CDCl₃): δ=7.29-7.24 (m, 2H), 7.24-7.19 (m, 1H), 7.16-7.12 (m, 2H), 6.85 (d, J=7.9 Hz, 1H), 6.74 (d, J=1.9 Hz, 1H), 6.72 (dd, J=8.0, 1.9 Hz, 1H), 5.57 (s, 1H), 4.30 (t, J=6.9 Hz, 2H), 3.84 (s, 3H), 3.51 (s, 2H), 2.91 (t, J=6.9 Hz, 2H).
¹³C-NMR (100 MHz, CDCl₃): δ=171.8, 146.4, 144.7, 137.7, 128.9 (2C), 128.4 (2C), 126.5, 125.7, 122.2, 114.3, 111.7, 65.3, 55.87, 41.1, 35.0.
GCMS: m/z (%)=286 [M⁺] (30), 182 (48), 137 (100), 122 (12), 105 (30), 94 (11), 77 (12), 65 (8), 51 (7), 39(5).

Pentyl-2-(4-hydroxy-3-methoxyphenyl) acetate (20, method A)

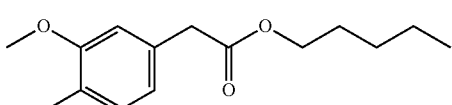

¹H-NMR (400 MHz, CDCl₃): δ=6.85 (d, J=8.0 Hz, 1H), 6.81 (d, J=2.0 Hz, 1H), 6.76 (dd, J=8.1, 2.0 Hz, 1H), 5.58 (s, 1H), 4.08 (t, J=6.7 Hz, 2H), 3.88 (s, 3H), 3.53 (s, 2H), 1.61 (q, J=6.7 Hz, 2H), 1.37-1.24 (m, 4H), 0.94-0.83 (m, 3H).
¹³C-NMR (100 MHz, CDCl₃): δ=172.0, 146.5, 144.7, 126.0, 122.1, 114.3, 111.7, 65.0, 55.9, 41.1, 28.3, 28.0, 22.3, 14.0.
GCMS: m/z (%)=252 [M⁺] (28), 182 (5), 137 (100), 122 (10), 94 (5), 66 (3), 43 (13), 29 (4).

Heptyl-2-(4-hydroxy-3-methoxyphenyl) acetate (14, method A)

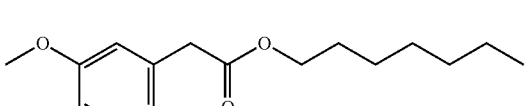

¹H-NMR (400 MHz, CDCl₃): δ=6.85 (dd, J=8.1, 1.1 Hz, 1H), 6.81 (t, J=1.4 Hz, 1H), 6.76 (dt, J=8.2, 1.4 Hz, 1H), 5.59 (d, J=1.1 Hz, 1H), 4.08 (td, J=6.8, 1.1 Hz, 2H), 3.88 (d, J=1.2 Hz, 3H), 3.53 (s, 2H), 1.68-1.55 (m, 2H), 1.28 (td, J=9.8, 9.3, 4.0 Hz, 8H), 0.94-0.82 (m, 3H).

$^{13}$C-NMR (100 MHz, CDCl$_3$): δ=172.0, 146.5, 144.7, 126.0, 122.1, 114.3, 111.7, 65.0, 55.9, 41.1, 31.7, 28.9, 28.6, 25.8, 22.6, 14.1.

GCMS: m/z (%)=280 [M$^+$] (34), 182 (12), 137 (100), 122 (8), 94 (5), 57 (11), 41 (8).

Alternatively, esters of homovanillic acid can also be obtained by transesterification, as shown by way of example on substance 2:

[(E)-Cinnamyl]-2-(4-hydroxy-3-methoxyphenyl) acetate (2)

Ethyl homovanillate (5 g) was mixed with cinnamyl alcohol (7.5 g) and 25% sodium methylate solution (0.52 g) and heated to 150-170° C., vacuum applied above approximately 130° C. and MeOH/EtOH distilled from the reaction mixture for 1-3 h. It was diluted with MTBE, the organic phase was washed once with saturated aqueous NH$_4$Cl solution and once with water and the solvent was removed under vacuum. Excess cinnamyl alcohol was then removed by distillation and the product was obtained by column chromatographic purification on silica gel or fractionated distillation with a yield of 40-50%.

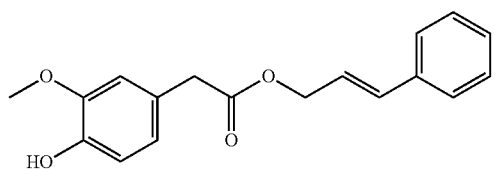

2

$^1$H NMR (400 MHz, CDCl$_3$): δ=7.38-7.35 (m, 2H), 7.35-7.29 (m, 2H), 7.29-7.23 (m, 1H), 6.87 (d, J=8.0 Hz, 1H), 6.82 (d, J=2.0 Hz, 1H), 6.79 (dd, J=8.0, 2.0 Hz, 1H), 6.60 (dt, J=15.9, 1.5 Hz, 1H), 6.27 (dt, J=15.9, 6.4 Hz, 1H), 5.56 (s, 1H), 4.75 (dd, J=6.4, 1.4 Hz, 2H), 3.86 (s, 3H), 3.59 (s, 2H).

$^{13}$C NMR (100 MHz, CDCl$_3$): δ=171.64, 146.48, 144.80, 136.15, 134.17, 128.60, 128.08, 126.58, 125.69, 123.02, 122.19, 114.38, 111.71, 65.34, 55.89, 40.99.

GCMS: m/z (%)=298 [M+] (12), 137 (100), 122 (8), 117 (68), 94 (8), 91 (12), 77 (4), 65 (4), 51 (4), 39(6).

Example 5: Tasting of Esters of Homovanillinic Acid

The substance to be tasted was dissolved in ethanol and the ethanolic solution was then diluted with 5% sugar solution (final concentration: 25 ppm). For the tasting, the oral cavity was rinsed and spat out by 4 tasters with approx. 5 ml of the sugar solution. The pungency was assessed on a scale of 1 (very weak)-9 (very strong) and the profile was assessed.

a) Profile of hexyl-2-(4-hydroxy-3-methoxyphenyl) acetate (21): clearly pungent, slightly delayed effect, warming, relatively fast decrease in pungency; pungency assessed at 9.

b) Profile of butyl-2-(4-hydroxy-3-methoxyphenyl) acetate (19): immediate pungency, quick decrease; pungency assessed at 7.

c) Profile of isobutyl-2-(4-hydroxy-3-methoxyphenyl) acetate (9): quick onset of pungency, warming, slightly biting pungency; pungency assessed at 4-5.

d) Profile of propyl-2-(4-hydroxy-3-methoxyphenyl) acetate (18): weak and delayed pungency, gradually warming, tingling; pungency assessed at 4-5.

e) Profile of ethyl-2-(4-hydroxy-3-methoxyphenyl) acetate (17): slightly warming, somewhat pungent; pungency assessed at 1-2.

f) Profile of isopropyl-2-(4-hydroxy-3-methoxyphenyl) acetate (7): Late onset, tingling, warming, pungent, somewhat delayed, not long-lasting, pleasant; pungency assessed at 3.

g) Profile of sec-butyl-2-(4-hydroxy-3-methoxyphenyl) acetate (8): very delayed onset, tingling, mainly warming, gradually increasing pungency, pungency assessed at 3.

h) Profile of octyl-2-(4-hydroxy-3-methoxy-phenyl) acetate (not according to the invention): slow onset of pungency, late, delayed, greasy-pulpy secondary effect, burning; pungency assessed at 7.

i) Profile of decyl-2-(4-hydroxy-3-methoxyphenyl) acetate (not according to the invention): weakly pungent, delayed, pear-like and greasy-pulpy secondary effect, throat burns more than the tongue; pungency assessed at 2.

k) 3-Phenylpropyl-2-(4-hydroxy-3-methoxyphenyl) acetate (22):2 ppm*: delayed effect, pungent, warming, slightly tingling; pungency assessed at 5.

l) 4-Phenylbutyl-2-(4-hydroxy-3-methoxyphenyl) acetate (23):2.5 ppm*: delayed effect, pungent, delayed warming, burning, slightly tingling; pungency assessed at 4-5.

m) [(E)-Cinnamyl]-2-(4-hydroxy-3-methoxyphenyl) acetate (2):1.5 ppm*: delayed effect, very pungent, slightly warming, somewhat mouthwatering; pungency assessed at 5-6.

n) Heptyl-2-(4-hydroxy-3-methoxyphenyl) acetate (14): 1.5 ppm*: slightly delayed effect, burning, pungent, warming, pungency assessed at 3.

*Owing to their strong pungency, these compounds were only tasted at final concentrations of 1.5-2.5 ppm.

Example 6: Isointensity of Esters of Homovanillinic Acid when Compared to Nonivamide and a *Capsicum* Extract The substance to be tasted was dissolved in ethanol and the ethanolic solution was then diluted with 5% sugar solution (final concentration: 10 ppm). As reference, *capsicum* extract with 1,000,000 SHU (0.3-10 ppm) and nonivamide (0.1-1 ppm) were prepared in 5% sugar solution in increasing concentration. For the tasting, the oral cavity was rinsed and spat out by 4 tasters with approx. 5 ml of the solution to be tasted and assessed against the reference series.

The pungency of 10 ppm of hexyl-2-(4-hydroxy-3-methoxyphenyl) acetate (21) is comparable to the one of 0.5 ppm nonivamide.

The pungency of 10 ppm of butyl-2-(4-hydroxy-3-methoxyphenyl) acetate (19) is comparable to the one of 0.3 ppm nonivamide.

The pungency of 10 ppm of butyl-2-(4-hydroxy-3-methoxyphenyl) acetate (19) is comparable to the one of 4.5 ppm *capsicum* extract with 1,000,000 SHU.

The pungency of 10 ppm of hexyl-2-(4-hydroxy-3-methoxyphenyl) acetate (21) is comparable to the one of 8.5 ppm *capsicum* extract with 1,000,000 SHU.

Example 7: Thresholds of the Esters of Homovanillinic Acid

The thresholds were determined according to ASTM E 679-91 ("Standard Practice for Determination of Odor and Taste Thresholds By a Forced-Choice Ascending Concentration Series Method of Limits1"). It is the respective flavour stimulus threshold to Vittel® water.

For example, the threshold of hexyl-2-(4-hydroxy-3-methoxyphenyl) acetate (21) in water is at 1.7 ppm (1700 ppb).

For example, the threshold of ethyl-2-(4-hydroxy-3-methoxyphenyl) acetate (17) in water is at 29.5 ppm (29460 ppb).

For example, the threshold of butyl-2-(4-hydroxy-3-methoxyphenyl) acetate (19) in water is at 3.5 ppm (3540 ppb).

Figure 3:
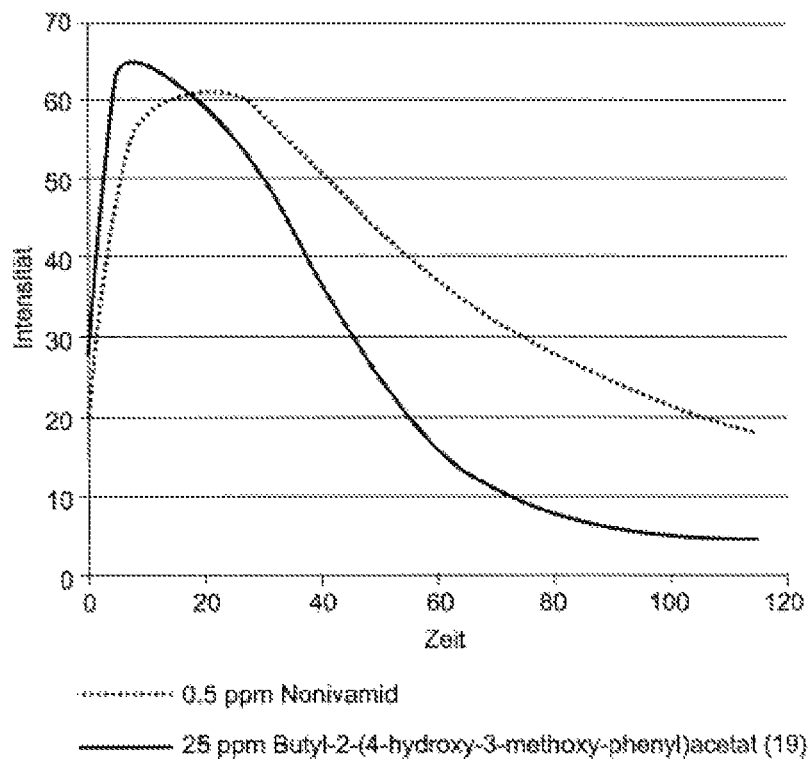
FIG. 3 is a graph of the pungency profile of butyl-2-(4-hydroxy-3-methoxyphenyl) acetate compared with nonivamide according to aspects of the invention.

Example 8: Pungency profile of butyl-2-(4-hydroxy-3-methoxyphenyl) acetate (19) compared with nonivamide To obtain a time vs. intensity profile, trained panelists (n=8-10) rinsed their oral cavity with a gulp of a sample solution (5 ml of a 5% sugar solution). Then, the intensity of the characteristic pungency was assessed at defined time intervals on the basis of a scale without fixed graduation. The two solutions to be tasted (butyl-2-(4-hydroxy-3-methoxyphenyl) acetate (19) with 25 ppm and nonivamide with 0.5 ppm of the corresponding substance were coded and placed in a mixed sequence. Between the two samples to be tasted, the oral cavity was neutralised with bread and water and pre-rinsing with 5 ml of 5% sugar solution. The data was analysed and graphically displayed as a time vs. intensity curve (see FIG. 3 (Pungency profile of butyl-2-(4-hydroxy-3-methoxyphenyl) acetate (19) compared with nonivamide).

The faster onset of the pungency of butyl-2-(4-hydroxy-3-methoxyphenyl) acetate (19) compared with nonivamide at identical total intensity as well as the considerably faster decrease in pungency could be clearly observed.

Example 9: Combination of Esters of Homovanillic Acid with Grains of Paradise Extract, Nonivamide and a *Capsicum* Extract Different combinations of ethyl-2-(4-hydroxy-3-methoxyphenyl) acetate (17) and butyl-2-(4-hydroxy-3-methoxyphenyl) acetate (19) with grains of paradise extract (PN 300953, Symrise), nonivamide and capsicum extract 1,000,000 SHU were subjected to sensorial assessment. The tasting solutions containing an ester of homovanillic acid at an increasing concentration (ppm) in combination with a trigeminal substance of a certain concentration, based on a 5% sugar solution (Tab. 3) were assessed by 3 testers. To this end, the oral cavity was rinsed with approx. 5 ml of the specific solution to be tasted and the solution was spat out again.

TABLE 3

Combinations of esters of homovanillic acid (HVE) with grains of paradise extract (PN 300953, Symrise), nonivamide and a capsicum extract (basis: 5% sugar solution, specifications in ppm).

| | Example | | | | | | | | | | | | | | | | |
|---|---|---|---|---|---|---|---|---|---|---|---|---|---|---|---|---|---|
| | 1* | 2 | 3 | 4 | 5 | 6* | 7 | 8 | 9 | 10 | 11* | 12 | 13 | 14 | 15 | 16* | 17 |
| Grains of paradise extract | 30 | 30 | 30 | 30 | 30 | — | — | — | — | — | — | — | — | — | — | — | — |
| Nonivamide | — | — | — | — | — | 0.2 | 0.2 | 0.2 | 0.2 | 0.2 | 0.5 | 0.5 | 0.5 | 0.5 | 0.5 | — | — |
| Capsicum extract | — | — | — | — | — | — | — | — | — | — | — | — | — | — | — | 2 | 2 |
| HVE 17 | — | 10 | 25 | — | — | — | 50 | 100 | — | — | — | 50 | 100 | — | — | — | 50 |
| HVE 19 | — | — | — | 3 | 7 | — | — | — | 15 | 30 | — | — | — | 15 | 30 | — | — |

| | Example | | | | | | | | | | | |
|---|---|---|---|---|---|---|---|---|---|---|---|---|
| | 18 | 19 | 20 | 21* | 22 | 23 | 24 | 25 | 26* | 27 | 28* | 29 |
| Grains of paradise extract | — | — | — | — | — | — | — | — | — | — | — | — |
| Nonivamide | — | — | — | — | — | — | — | — | 0.1 | 0.1 | 0.2 | 0.2 |
| Capsicum extract | 2 | 2 | 2 | 5 | 5 | 5 | 5 | 5 | 5 | 5 | 2 | 2 |
| HVE 17 | 100 | — | — | — | 50 | 100 | — | — | — | — | — | 50 |
| HVE 19 | — | 10 | 25 | — | — | — | 10 | 25 | — | 10 | — | — |

*not according to the invention

Esters of homovanillic acid have an intensifying effect on the used compounds. A faster onset of the pungency was detected for the combination of grains of paradise extract (PN 300953, Symrise) with ethyl-2-(4-hydroxy-3-methoxyphenyl) acetate (17, examples 2 and 3). In the combination of ethyl-2-(4-hydroxy-3-methoxyphenyl) acetate (17) with nonivamide (examples 7 and 8 as well as 12 and 13), the pungency of nonivamide was intensified at both of the tested concentrations, wherein this intensification corresponded to more than just the additive effect. Furthermore, a faster onset of the pungency was detected. The same intensifying and faster onsetting effect was also detected in the combination of ethyl-2-(4-hydroxy-3-methoxyphenyl) acetate (17) with 2 ppm *capsicum* extract with 1,000,000 SHU (examples 17 and 18), wherein the pungency sensation was assessed as being pleasant and not long-lasting. In the absence of combination with a homovanillyl ester, the onset of the pungency of the *capsicum* extract with 1,000,000 SHU was perceived only with a delay (examples 16* and 21*). The intensification of the pungency was significantly higher with 2 ppm *capsicum* extract with 1,000,000 SHU than with 5 ppm. In the combination of 5 ppm *capsicum* extract with 1,000,000 SHU with different amounts of ethyl-2-(4-hydroxy-3-methoxyphenyl) acetate (17, examples 22 and 23), quick decline in the pungency was apparent. In addition, the pungency of *capsicum* extract with 1,000,000 SHU in the combination with ethyl-2-(4-hydroxy-3-methoxyphenyl) acetate (17) at all concentrations was complemented by a pleasantly warming effect, which remained even after the pungency sensation receded. For butyl-2-(4-hydroxy-3-methoxyphenyl) acetate (19), the same effects were detected even at lower concentrations (examples 19 and 20 as well as 24 and 25), wherein the intensifications were more significant than just an additive effect. Also a combination of nonivamide, *capsicum* extract with 1,000,000 SHU and ethyl-2-(4-hydroxy-3-methoxyphenyl) acetate (17, example 27) or butyl-2-(4-hydroxy-3-methoxyphenyl) acetate (19, example 29) also showed quicker decline in the pungency sensation as well as a warming effect for the combinations without esters of homovanillic acid (examples 26* and 28*).

Example 10: Increase in the alcohol pungency of an ethanolic solution by ethyl-2-(4-hydroxy-3-methoxyphenyl) acetate (17)

On the basis of a 5% sugar solution with 20% ethanol (example 1), different concentrations (10-100 ppm) of ethyl-2-(4-hydroxy-3-methoxyphenyl) acetate (17), polymethoxylated flavone PMF 60 (Miritz) and combinations (10-50 ppm) of ethyl-2-(4-hydroxy-3-methoxyphenyl) acetate (17) with polymethoxylated flavone PMF 60 (Miritz) (20 ppm) were compared with a second base solution (5% sugar solution with 40% ethanol) (Tab. 4). To this end, 5 testers rinsed their mouth with about 5 ml of the relevant solution to be tasted, spat out the solution and assessed the taste sensation.

TABLE 4

Combinations of ethyl-2-(4-hydroxy-3-methoxyphenyl) acetate (17) and polymethoxylated flavone PMF 60 (Miritz) in a 5% sugar solution with 20% ethanol (specifications in ppm).

| Ingredient | 1* | 2 | 3 | 4 | 5 | 6* | 7 | 8 | 9 |
|---|---|---|---|---|---|---|---|---|---|
| Ethyl-2-(4-hydroxy-3-methoxyphenyl) acetate (17) | — | 10 | 20 | 50 | 100 | — | 10 | 20 | 50 |

TABLE 4-continued

Combinations of ethyl-2-(4-hydroxy-3-methoxyphenyl) acetate (17) and polymethoxylated flavone PMF 60 (Miritz) in a 5% sugar solution with 20% ethanol (specifications in ppm).

| Ingredient | 1* | 2 | 3 | 4 | 5 | 6* | 7 | 8 | 9 |
|---|---|---|---|---|---|---|---|---|---|
| Polymethoxylated flavone PMF 60 | — | — | — | — | — | 20 | 20 | 20 | 20 |

*not according to the invention

The base solution (5% sugar solution with 20% ethanol, example 1) was described as alcoholic, burning. The addition of ethyl-2-(4-hydroxy-3-methoxyphenyl) acetate (17, example 2) led to an increase and an extension of the burning sensation in the mouth. Further increase to 20 ppm and 50 ppm (examples 2-5) resulted in an additional pungency effect. Polymethoxylated flavone PMF 60 on its own (example 6) resulted in an increase of the alcoholic taste in the tasting solution, but not a burning sensation in the mouth compared to example 1. This taste was increased by means of the combination with ethyl-2-(4-hydroxy-3-methoxyphenyl) acetate (17, examples 7-9), an increase of the burning sensation was additionally generated, and an extension of these effects was also achieved, whereby the use of 20-50 ppm ethyl-2-(4-hydroxy-3-methoxyphenyl) acetate (17) was sensorially preferred. Compared to the second base solution (5% sugar solution with 40% ethanol) with a higher alcohol content and a high nasal effect, this combination did not show any nasal effect.

Example 11: Warming Effect of Esters of Homovanillic Acid Compared to Vanillyl Butyl Ether Test solutions with 4-10 ppm ester of homovanillic acid were sensorially evaluated in a 5% sugar solution and were compared to a test solution of 10 ppm vanillyl butyl ether. Ethyl-2-(4-hydroxy-3-methoxyphenyl) acetate (17) had a milder warming effect compared to vanillyl butyl ether. Butyl-2-(4-hydroxy-3-methoxyphenyl) acetate (19) had a more marked warming effect than vanillyl butyl ether. Isobutyl-2-(4-hydroxy-3-methoxyphenyl) acetate (9) showed a warming effect similar to vanillyl butyl ether, but which lasted for a longer period. Propyl-2-(4-hydroxy-3-methoxyphenyl) acetate (18) also showed a long-lasting warming effect, but which occurred at a comparatively later time.

APPLICATION EXAMPLES

Application Example 1: Typically Pungent Flavour Compositions, Containing Esters of Homovanillic Acid The following were mixed (all specifications in % w/w, unless specified otherwise):

| Ingredient | A | B | C | D | E | F | G | H |
|---|---|---|---|---|---|---|---|---|
| 10% w/w pellitorine in 1,2-propylene glycol/ diethyl | 0.25 | 0.25 | 0.25 | 0.25 | 0.25 | 0.25 | 0.25 | 0.25 |
| Hesperetin | 2.50 | 2.50 | 2.50 | 2.50 | 2.50 | 2.50 | 2.50 | 2.50 |
| Phloretin | 1.50 | 1.50 | 1.50 | 1.50 | 1.50 | 1.50 | 1.50 | 1.50 |
| Ethyl-2-(4-hydroxy-3-methoxyphenyl) acetate (17) | 3.00 | — | 1.50 | 100 | — | — | — | — |
| Butyl-2-(4-hydroxy-3-methoxyphenyl) acetate (19) | — | 0.50 | 0.25 | — | — | — | — | — |

-continued

| Ingredient | A | B | C | D | E | F | G | H |
|---|---|---|---|---|---|---|---|---|
| Propyl-2-(4-hydroxy-3-nnethoxyphenyl) acetate (18) | — | — | — | 1.50 | — | — | 100 | — |
| 3-phenylpropyl 2-(4-hydroxy-3-methoxyphenyl) acetate (22) | — | — | — | — | 0.05 | — | — | — |
| 4-phenylbutyl 2-(4-hydroxy-3-methoxyphenyl) acetate (23) | — | — | — | — | — | 0.07 | — | — |
| Heptyl-2-(4-hydroxy-3-methoxyphenyl) acetate (14) | — | — | — | — | — | — | 0.10 | — |
| [(E)-cinnamyl]-2-(4-hydroxy-3-methoxyphenyl) acetate (2) | — | — | — | — | — | — | — | 0.06 |
| Propylene glycol | ad 100 | ad 100 | ad 100 | ad 100 | ad 100 | ad 100 | ad 100 | ad 100 |

The ingredients (substances or solutions) are mixed in the above-specified quantity ratios and then taken up in propylene glycol and dissolved completely by slight warming.

Application Example 2: Spray-Dried Flavour Compositions, Containing Esters of Homovanillic Acid The following were mixed (all specifications in % w/w, unless specified otherwise):

| Ingredient | A | B | C | D | E | F | G | H |
|---|---|---|---|---|---|---|---|---|
| Ethyl-2-(4-hydroxy-3-methoxyphenyl) acetate (17) | 10.00 | — | — | — | — | — | — | — |
| Butyl-2-(4-hydroxy-3-methoxyphenyl) acetate (19) | — | 3.50 | — | — | — | — | — | — |
| Propyl-2-(4-hydroxy-3-methoxyphenyl) acetate (18) | — | — | 5.00 | — | — | — | — | — |
| Hexyl-2-(4-hydroxy-3-methoxyphenyl) acetate (21) | — | — | — | 2.50 | — | — | — | — |
| 3-phenylpropyl 2-(4-hydroxy-3-methoxyphenyl) acetate (22) | — | — | — | — | 0.20 | — | — | — |
| 4-phenylbutyl 2-(4-hydroxy-3-methoxyphenyl) acetate (23) | — | — | — | — | — | 0.22 | — | — |
| Heptyl-2-(4-hydroxy-3-methoxyphenyl) acetate (14) | — | — | — | — | — | — | 0.25 | — |
| [(E)-cinnamyl]-2-(4-hydroxy-3-methoxyphenyl) acetate (2) | — | — | — | — | — | — | — | 0.21 |
| Maltodextrin | ad 100 | ad 100 | ad 100 | ad 100 | ad 100 | ad 100 | ad 100 | ad 100 |

The two components are dissolved in a mixture of ethanol and demineralised water and are spray-dried afterwards.

Application Example 3: Preparation of Mouthwash Flavours Using the Above-Described Flavourings The following were mixed (all specifications in % w/w, unless specified otherwise):

| Ingredient | A | B | C | D | E | F | G | H | I |
|---|---|---|---|---|---|---|---|---|---|
| Anethole | 30 | 30 | 30 | 30 | 30 | 30 | 30 | 30 | 30 |
| Eucalyptol | 25 | 25 | 25 | 25 | 25 | 25 | 25 | 25 | 25 |
| L-Menthol | 36.00 | 36.00 | 38.00 | 36.20 | 36.00 | 36.90 | 39.85 | 34.90 | 39.90 |
| Optacool A | — | 8 | — | 8 | — | 8 | — | 8 | — |
| Coolact 10 | 5 | — | 5 | — | 5 | — | 5 | — | 5 |
| Ethyl-2-(4-hydroxy-3-methoxyphenyl) acetate (17) | 4.00 | — | — | — | 3.00 | — | — | 2.00 | — |
| Butyl-2-(4-hydroxy-3-methoxyphenyl) acetate (19) | — | 1.00 | — | — | — | — | — | — | — |
| Propyl-2-(4-hydroxy-3-methoxyphenyl) acetate (18) | — | — | 2.00 | — | 1.00 | — | — | — | — |

-continued

| Ingredient | A | B | C | D | E | F | G | H | I |
|---|---|---|---|---|---|---|---|---|---|
| Hexyl-2-(4-hydroxy-3-methoxyphenyl) acetate (21) | — | — | — | 0.80 | — | — | — | — | — |
| 3-phenylpropyl 2-(4-hydroxy-3-methoxyphenyl) acetate (22) | — | — | — | — | — | 0.10 | — | — | — |
| 4-phenylbutyl 2-(4-hydroxy-3-methoxyphenyl) acetate (23) | — | — | — | — | — | — | 0.15 | — | — |
| Heptyl-2-(4-hydroxy-3-methoxyphenyl) acetate (14) | — | — | — | — | — | — | — | 0.10 | — |
| [(E)-cinnamyl]-2-(4-hydroxy-3-methoxyphenyl) acetate (2) | — | — | — | — | — | — | — | — | 0.10 |
| Total | 100 | 100 | 100 | 100 | 100 | 100 | 100 | 100 | 100 |

Application Example 4: Production of Flavourings with Peppermint Taste Using Substances According to the Invention The following were mixed (all specifications in % w/w, unless specified otherwise):

| Ingredient | A | B | C | D | E | F | G | H | I | K |
|---|---|---|---|---|---|---|---|---|---|---|
| Peppermint oil Mentha arvensis | 56 | 59.00 | 58.50 | 58.80 | 56 | 59 | 60 | 60 | 59.5 | 60 |
| L-Menthone | 20 | 20 | 20 | 20 | 20 | 20 | 20 | 20 | 20 | 20 |
| L-Menthol | 20 | 20 | 20 | 20 | 20 | 20 | 20 | 20 | 20 | 20 |
| Ethyl-2-(4-hydroxy-3-methoxyphenyl) acetate (17) | 4.00 | — | — | — | 3.00 | — | — | — | — | — |
| Butyl-2-(4-hydroxy-3-methoxyphenyl) acetate (19) | — | 1.00 | — | — | — | 0.50 | — | — | 0.50 | — |
| Propyl-2-(4-hydroxy-3-methoxyphenyl) acetate (18) | — | — | 1.50 | — | 1.00 | 0.50 | — | — | — | — |
| Pentyl-2-(4-hydroxy-3-methoxyphenyl) acetate (20) | — | — | — | 1.20 | — | — | — | — | — | — |
| 3-phenylpropyl 2-(4-hydroxy-3-methoxyphenyl) acetate (22) | — | — | — | — | — | — | 0.20 | — | — | — |
| 4-phenylbutyl 2-(4-hydroxy-3-methoxyphenyl) acetate (23) | — | — | — | — | — | — | — | 0.22 | — | — |
| Heptyl-2-(4-hydroxy-3-methoxyphenyl) acetate (14) | — | — | — | — | — | — | — | — | 0.25 | — |
| [(E)-cinnamyl]-2-(4-hydroxy-3-methoxyphenyl) acetate (2) | — | — | — | — | — | — | — | — | — | 0.21 |
| Total | 100 | 100 | 100 | 100 | 100 | 100 | 100 | 100 | 100 | 100 |

The flavour compositions were used in the below-described application examples.

Application Example 5: Alcohol-Reduced Beverage

Production of a beer mixed drink with reduced alcohol content or without alcohol. All specifications are in % w/w.

| Ingredient | A* | B | C | D | E | F | G | H | I |
|---|---|---|---|---|---|---|---|---|---|
| Sugar syrup | 4 | 4 | 4 | 4 | 4 | 4 | 4 | 4 | 4 |
| Beer (4.9% v/v) | 50 | — | — | — | — | — | — | — | — |
| Beer (with reduced alcohol and calories, 2.8% v/v) | — | — | 50 | — | 50 | — | 50 | — | 50 |
| Beer (alcohol-free, 0%) | — | 50 | — | 50 | — | 50 | — | 50 | — |
| Citric acid | 0.15 | 0.15 | 0.15 | 0.15 | 0.15 | 0.15 | 0.15 | 0.15 | 0.15 |
| Ascorbic acid | 0.01 | 0.01 | 0.01 | 0.01 | 0.01 | 0.01 | 0.01 | 0.01 | 0.01 |
| Grapefruit juice | 6 | 6 | 6 | 6 | 6 | 6 | 6 | 6 | 6 |
| Grapefruit flavour | 0.20 | 0.20 | 0.20 | 0.20 | 0.20 | 0.20 | 0.20 | 0.20 | 0.20 |

-continued

| Ingredient | A* | B | C | D | E | F | G | H | I |
|---|---|---|---|---|---|---|---|---|---|
| Flavour preparation (application example 1A) | — | 0.20 | 0.20 | — | — | — | — | — | — |
| Flavour preparation (application example 1B) | — | — | — | 0.20 | 0.20 | — | — | — | — |
| Flavour preparation (application example 1E) | — | — | — | — | — | 0.20 | 0.20 | — | — |
| Flavour preparation (application example 1H) | — | — | — | — | — | — | — | 0.20 | 0.20 |
| Water | ad 100 | ad 100 | ad 100 | ad 100 | ad 100 | ad 100 | ad 100 | ad 100 | ad 100 |
| Carbon dioxide | 0.70 | 0.70 | 0.70 | 0.70 | 0.70 | 0.70 | 0.70 | 0.70 | 0.70 |

*not according to the invention

Application Example 6: Applications in a Toothpaste ("Silica Opaque")

All specifications in % w/w, unless specified otherwise.

| Ingredient | A | B | C | D | E | F | G | H | I | K |
|---|---|---|---|---|---|---|---|---|---|---|
| Deionised water | 26.53 | 26.53 | 26.53 | 26.53 | 26.53 | 26.53 | 26.53 | 26.53 | 26.53 | 26.53 |
| Sorbitol 70% | 45 | 44.975 | 45 | 44.975 | 45 | 44.975 | 45 | 44.975 | 45 | 44.975 |
| Solbrol M sodium salt | 0.15 | 0.15 | 0.15 | 0.15 | 0.15 | 0.15 | 0.15 | 0.15 | 0.15 | 0.15 |
| Trisodium phosphate | 0.10 | 0.10 | 0.10 | 0.10 | 0.10 | 0.10 | 0.10 | 0.10 | 0.10 | 0.10 |
| Saccharin | 0.20 | 0.20 | 0.20 | 0.20 | 0.20 | 0.20 | 0.20 | 0.20 | 0.20 | 0.20 |
| Sodium monofluorophosphate | 1.12 | 1.12 | 1.12 | 1.12 | 1.12 | 1.12 | 1.12 | 1.12 | 1.12 | 1.12 |
| PEG 1500 | 5 | 5 | 5 | 5 | 5 | 5 | 5 | 5 | 5 | 5 |
| Sident 9 (abrasive silica) | 10 | 10 | 10 | 10 | 10 | 10 | 10 | 10 | 10 | 10 |
| Sident 22 S (thickening silica) | 8 | 8 | 8 | 8 | 8 | 8 | 8 | 8 | 8 | 8 |
| Sodium carboxymethyl cellulose | 0.90 | 0.90 | 0.90 | 0.90 | 0.90 | 0.90 | 0.90 | 0.90 | 0.90 | 0.90 |
| Titanium (IV) oxide | 0.50 | 0.50 | 0.50 | 0.50 | 0.50 | 0.50 | 0.50 | 0.50 | 0.50 | 0.50 |
| Sodium lauryl sulphate (SLS) | 1.50 | 1.50 | 1.50 | 1.50 | 1.50 | 1.50 | 1.50 | 1.50 | 1.50 | 1.50 |
| Pellitorine solution PLM (containing 10% pellitorine) | — | 0.025 | — | 0.025 | — | 0.025 | — | 0.025 | — | 0.025 |
| Peppermint flavour type (application example 4A) | 1.00 | 1.00 | — | — | — | — | — | — | — | — |
| Peppermint flavour type (application example 4B) | — | — | 1.00 | 1.00 | — | — | — | — | — | — |
| Peppermint flavour type (application example 4C) | — | — | — | — | 1.00 | 1.00 | — | — | — | — |
| Peppermint flavour type (application example 4G) | — | — | — | — | — | — | 1.00 | 1.00 | — | — |
| Peppermint flavour type (application example 4K) | — | — | — | — | — | — | — | — | 1.00 | 1.00 |
| Total | 100 | 100 | 100 | 100 | 100 | 100 | 100 | 100 | 100 | 100 |

Application Example 7: Application in a Toothpaste (Calcium Carbonate Base)

All specifications in % w/w, unless specified otherwise.

| Ingredient | A | B | C | D | E | F | G | H | I | K |
|---|---|---|---|---|---|---|---|---|---|---|
| Deionised water | 27.5 | 27.48 | 27.5 | 27.48 | 27.5 | 27.48 | 27.5 | 27.48 | 27.5 | 27.48 |
| Saccharin | 0.20 | 0.20 | 0.20 | 0.20 | 0.20 | 0.20 | 0.20 | 0.20 | 0.20 | 0.20 |
| Solbrol M sodium salt | 0.20 | 0.20 | 0.20 | 0.20 | 0.20 | 0.20 | 0.20 | 0.20 | 0.20 | 0.20 |
| Sodium monofluorophosphate | 0.80 | 0.80 | 0.80 | 0.80 | 0.80 | 0.80 | 0.80 | 0.80 | 0.80 | 0.80 |

-continued

| Ingredient | A | B | C | D | E | F | G | H | I | K |
|---|---|---|---|---|---|---|---|---|---|---|
| Sorbitol 70% | 29 | 29 | 29 | 29 | 29 | 29 | 29 | 29 | 29 | 29 |
| Calcium carbonate | 35 | 35 | 35 | 35 | 35 | 35 | 35 | 35 | 35 | 35 |
| Sident 22 S (thickening silica) | 2.50 | 2.50 | 2.50 | 2.50 | 2.50 | 2.50 | 2.50 | 2.50 | 2.50 | 2.50 |
| Sodium carboxymethyl cellulose | 1.30 | 1.30 | 1.30 | 1.30 | 1.30 | 1.30 | 1.30 | 1.30 | 1.30 | 1.30 |
| Titanium dioxide | 0.50 | 0.50 | 0.50 | 0.50 | 0.50 | 0.50 | 0.50 | 0.50 | 0.50 | 0.50 |
| Sodium lauryl sulphate | 2 | 2 | 2 | 2 | 2 | 2 | 2 | 2 | 2 | 2 |
| Pellitorine solution PLM (containing 10% pellitorine) | — | 0.02 | — | 0.02 | — | 0.02 | — | 0.02 | — | 0.02 |
| Peppermint flavour type (application example 4D) | 1.00 | 1.00 | — | — | — | — | — | — | — | — |
| Peppermint flavour type (application example 4E) | — | — | 1.00 | 1.00 | — | — | — | — | — | — |
| Peppermint flavour type (application example 4F) | — | — | — | — | 1.00 | 1.00 | — | — | — | — |
| Peppermint flavour type (application example 4H) | — | — | — | — | — | — | 1.00 | 1.00 | — | — |
| Peppermint flavour type (application example 4I) | — | — | — | — | — | — | — | — | 1.00 | 1.00 |
| Total | 100 | 100 | 100 | 100 | 100 | 100 | 100 | 100 | 100 | 100 |

By means of using the substances according to the invention, a quickly onsetting pleasant feeling of pungency with warming aspects is achieved. Additionally, an increased mouthwatering effect is achieved.

Application Example 8: Application in a Sugar-Free Chewing Gum

| Part | Ingredient | wt % |
|---|---|---|
| A | Chewing gum, company "Jagum T" | 30.00 |
| B | Sorbitol, pulverised | 39.00 |
|  | Isomalt ® (Palatinit GmbH) | 9.50 |
|  | Xylitol | 2.00 |

-continued

| Part | Ingredient | wt % |
|---|---|---|
|  | Mannitol | 3.00 |
|  | Aspartame ® | 0.10 |
|  | Acesulfam ® K | 0.10 |
|  | Emulgum ® (Colloides Naturels, Inc.) | 0.30 |
| C | Sorbitol 70% | 14.00 |
|  | Glycerine | 1.00 |
| D | Flavour compositions according to example 4) | 1.00 |

Parts A to D are mixed and kneaded intensively. The obtained raw mass can then be processed to ready-to-eat chewing gums, e.g. in the form of thin strips.

Application Example 9: Mouthwash ("Ready to Use" without Alcohol)

| Ingredient | A | B | C | D | E | F | G | H | I | K |
|---|---|---|---|---|---|---|---|---|---|---|
| Cremophor RH 455 | 1.80 | 1.80 | 1.80 | 1.80 | 1.80 | 1.80 | 1.80 | 1.80 | 1.80 | 1.80 |
| Deionised water | 87.57 | 87.5575 | 87.57 | 87.5575 | 87.57 | 87.5575 | 87.57 | 87.5575 | 87.57 | 87.5575 |
| Sorbitol 70% | 10 | 10 | 10 | 10 | 10 | 10 | 10 | 10 | 10 | 10 |
| Sodium fluoride | 0.18 | 0.18 | 0.18 | 0.18 | 0.18 | 0.18 | 0.18 | 0.18 | 0.18 | 0.18 |
| Sodium saccharin 450 | 0.10 | 0.10 | 0.10 | 0.10 | 0.10 | 0.10 | 0.10 | 0.10 | 0.10 | 0.10 |
| Solbrol M sodium salt | 0.15 | 0.15 | 0.15 | 0.15 | 0.15 | 0.15 | 0.15 | 0.15 | 0.15 | 0.15 |
| Pellitorine solution PLM (containing 10% pellitorine) | — | 0.0125 | — | 0.0125 | — | 0.0125 | — | 0.0125 | — | 0.0125 |
| Mouthwash flavour (application example 3A) | 0.20 | 0.20 | — | — | — | — | — | — | — | — |
| Mouthwash flavour | — | — | 0.20 | 0.20 | — | — | — | — | — | — |

| Ingredient | A | B | C | D | E | F | G | H | I | K |
|---|---|---|---|---|---|---|---|---|---|---|
| (application example 3B) Mouthwash flavour (application example 3C) | — | — | — | — | 0.20 | 0.20 | — | — | — | — |
| Mouthwash flavour (application example 3F) | — | — | — | — | — | — | 0.20 | 0.20 | — | — |
| Mouthwash flavour (application example 3D) | — | — | — | — | — | — | — | — | 0.20 | 0.20 |
| Total | 100 | 100 | 100 | 100 | 100 | 100 | 100 | 100 | 100 | 100 |

Application Example 10: Toothpaste and Mouthwash as 2-in-1 Product

All specifications are in % w/w.

| Ingredient | A | B | C | D | E | F | G |
|---|---|---|---|---|---|---|---|
| Ethanol, 96% | 5 | 5 | 5 | 5 | 5 | 5 | 5 |
| Sorbitol, 70% in water | 40 | 40 | 40 | 40 | 40 | 40 | 40 |
| Glycerin | 20 | 20 | 20 | 20 | 20 | 20 | 20 |
| Saccharin | 0.20 | 0.20 | 0.20 | 0.20 | 0.20 | 0.20 | 0.20 |
| Sodium monofluorophosphate | 0.76 | 0.76 | 0.76 | 0.76 | 0.76 | 0.76 | 0.76 |
| Solbrol M, sodium salt | 0.15 | 0.15 | 0.15 | 0.15 | 0.15 | 0.15 | 0.15 |
| Abrasive silica (Sident 9) | 20 | 20 | 20 | 20 | 20 | 20 | 20 |
| Thickening silica (Sident 22S) | 2 | 2 | 2 | 2 | 2 | 2 | 2 |
| Sodium carboxymethyl cellulose | 0.30 | 0.30 | 0.30 | 0.30 | 0.30 | 0.30 | 0.30 |
| Sodium lauryl sulphate | 1.20 | 1.20 | 1.20 | 1.20 | 1.20 | 1.20 | 1.20 |
| Green dye (1% in water) | 0.50 | 0.50 | 0.50 | 0.50 | 0.50 | 0.50 | 0.50 |
| Distilled water | 9.39 | 9.39 | 9.39 | 9.39 | 8.89 | 8.89 | 8.89 |
| Flavour preparation (Application example 3A) | 0.50 | — | — | — | — | — | — |
| Flavour preparation (Application example 3B) | — | 0.50 | — | — | — | — | — |
| Flavour preparation (Application example 3C) | — | — | 0.50 | — | — | — | — |
| Flavour preparation (Application example 3D) | — | — | — | 0.50 | — | — | — |
| Flavour preparation (Application example 3F) | — | — | — | — | 1.00 | — | — |
| Flavour preparation (Application example 3H) | — | — | — | — | — | 1.00 | — |
| Flavour preparation (Application example 3I) | — | — | — | — | — | — | 1.00 |
| Total | 100 | 100 | 100 | 100 | 100 | 100 | 100 |

Application Example 11: Application in Combination with a Pungent Plant Extract as Alcohol Enhancer Reference Sample Liqueur Base 10% v/v

| 7.39 kg | alcohol, p.A. |
|---|---|
| 20 kg | inverted sugar syrup, 66.5% dry mass |
| 72.61 kg | water |
| Total 100 kg | |

Liqueur Base 5.5% v/v

| 4.06 kg | alcohol, p.A. |
|---|---|
| 20 kg | inverted sugar syrup, 66.5% dry mass |
| 75.94 kg | water |
| Total 100 kg | |

Version A: liqueur base 5.5% v/v+0.3% of a 10% solution of an extract of grains of paradise in ethanol Version B: liqueur base 5.5% v/v+0.075% of a 10% solution of an extract of grains of paradise in ethanol+0.2% of a solution of 1% ethyl-2-(4-hydroxy-3-methoxyphenyl) acetate (17) in ethanol (corresponds to 20 ppm).

Version C: liqueur base 5.5% v/v+0.075% of a 10% solution of an extract of grains of paradise in ethanol+0.01% of a solution of 1% ethyl-2-(4-hydroxy-3-methoxyphenyl) acetate (17) in ethanol (corresponds to 1 ppm).

In the versions B and C, the alcohol pungency of the reference sample is sensorially imitated better than in version A. Version A and the reference sample are sensorially evaluated as being very similar.

Application Example 12: Foot Balm

|   | % w/w | Ingredient (INCI) |
|---|---|---|
| A | 2.00 | Ceteareth-6, stearyl alcohol |
|   | 2.00 | Ceteareth-25 |
|   | 5.00 | Cetearyl ethyl hexanoate |
|   | 4.00 | Cetyl alcohol |
|   | 4.00 | Glyceryl stearate |
|   | 5.00 | Mineral oil |
|   | 0.20 | Menthol |
|   | 0.50 | Camphor |
| B | 69.30 | Demineralised water |
|   | q.s. | Preservative |
| C | 1.00 | Bisabolol |
|   | 1.00 | Tocopheryl acetate |
| D | 1.00 | Aqueous solution with 1-1.5% pentyl-2-(4-hydroxy-3-methoxyphenyl) acetate (20) |
|   | 5.00 | Witch hazel extract |
|   | 100 | Total |

Preparation: Heat the components of phases A and B separately to about 80'C. Stir phase B intro phase A while homogenising. Cool to about 40° C. while stirring, add the phases C and D and shortly homogenise again. Cool to room temperature while stirring.

Application Example 13: Sugar-Free Hard Caramels

| Ingredient | Content [% w/w] |
|---|---|
| Palatinite, type M | 75.47 |
| Water | 24.03 |
| Peppermint flavour | 0.10 |
| Flavour preparation (example 1) | 0.40 |
| Total | 100 |

At first, palatinite was mixed with water. The mixture was then melted at 165° C. and subsequently cooled to 115° C. The peppermint flavour and the flavour preparation (example 1) were then added. The mixtures were poured into moulds after mixing, removed from the moulds after solidifying, and then packaged individually.

Application Example 14: Spice Mix, Type "Pepper"

A=Reference preparation
B, C, D, E=Preparations according to the invention
All specifications are in % w/w.

| Ingredient | A* | B | C | D | E | F | G |
|---|---|---|---|---|---|---|---|
| Milk protein | 0.80 | 0.80 | 0.80 | 0.80 | 0.80 | 0.80 | 0.80 |
| Locust bean gum powder | 2.00 | 2.00 | 2.00 | 2.00 | 2.00 | 2.00 | 2.00 |
| Corn starch | 24.00 | 23.00 | 23.00 | 23.00 | 23.00 | 23.00 | 23.00 |
| Cooking salt | 14.00 | 14.00 | 14.00 | 14.00 | 14.00 | 14.00 | 14.00 |
| Bell pepper powder | 12.00 | 12.00 | 12.00 | 12.00 | 12.00 | 12.00 | 12.00 |
| Tomato powder | 12.00 | 12.00 | 12.00 | 12.00 | 12.00 | 12.00 | 12.00 |
| Sucrose | 4.00 | 4.00 | 4.00 | 4.00 | 4.00 | 4.00 | 4.00 |
| Garlic powder | 0.50 | 0.50 | 0.50 | 0.50 | 0.50 | 0.50 | 0.50 |
| Hardened vegetable fat | 8.00 | 8.00 | 8.00 | 8.00 | 8.00 | 8.00 | 8.00 |
| Fat powder | 11.00 | 11.00 | 11.00 | 11.00 | 11.00 | 11.00 | 11.00 |
| Sodium glutamate | 6.00 | 6.00 | 6.00 | 6.00 | 6.00 | 6.00 | 6.00 |
| Food dye beetroot and bell pepper | 2.00 | 2.00 | 2.00 | 2.00 | 2.00 | 2.00 | 2.00 |
| Flavour type "pepper" | 2.00 | 2.00 | 2.00 | 2.00 | 2.00 | 2.00 | 2.00 |
| Flavour type "pizza" | 1.20 | 1.20 | 1.20 | 1.20 | 1.20 | 1.20 | 1.20 |
| Flavour type "tomato" | 0.40 | 0.40 | 0.40 | 0.40 | 0.40 | 0.40 | 0.40 |
| Extract from black pepper | 0.10 | 0.10 | 0.10 | 0.10 | 0.10 | 0.10 | 0.10 |
| Flavour preparation (application example 1A) | — | 1.00 | — | — | — | — | — |
| Flavour preparation (application example 1B) | — | — | 1.00 | — | — | — | — |
| Flavour preparation (application example 1C) | — | — | — | 1.00 | — | — | — |
| Flavour preparation (application example 1D) | — | — | — | — | 1.00 | — | — |
| Flavour preparation (application example 1E) | — | — | — | — | — | 1.00 | — |
| Flavour preparation (application example 1G) | — | — | — | — | — | — | 1.00 |
| Total | 100 | 100 | 100 | 100 | 100 | 100 | 100 |

*not according to the invention

Application Example 15: Spice Mix for Potato Crisps

A=Reference preparation
B, C, D, E=Preparations according to the invention
All specifications are in % w/w.

| Ingredient | A* | B | C | D | E | F | G |
|---|---|---|---|---|---|---|---|
| Sodium glutamate | 3.50 | 3.50 | 3.50 | 3.50 | 3.50 | 3.50 | 3.50 |
| Cheese powder | 10.00 | 10.00 | 10.00 | 10.00 | 10.00 | 10.00 | 10.00 |
| Garlic powder | 2.00 | 2.00 | 2.00 | 2.00 | 2.00 | 2.00 | 2.00 |
| Whey powder | 38.86 | 36.86 | 36.86 | 36.86 | 36.86 | 36.86 | 36.86 |
| Spice extract oil | 0.20 | 0.20 | 0.20 | 0.20 | 0.20 | 0.20 | 0.20 |
| Bell pepper powder | 9.80 | 9.80 | 9.80 | 9.80 | 9.80 | 9.80 | 9.80 |
| Cooking salt | 21.00 | 21.00 | 21.00 | 21.00 | 21.00 | 21.00 | 21.00 |
| Tomato powder | 9.00 | 9.00 | 9.00 | 9.00 | 9.00 | 9.00 | 9.00 |
| Dry flavouring | 2.50 | 2.50 | 2.50 | 2.50 | 2.50 | 2.50 | 2.50 |
| Silicon dioxide | 0.02 | 0.02 | 0.02 | 0.02 | 0.02 | 0.02 | 0.02 |
| Vegetable oil | 0.02 | 0.02 | 0.02 | 0.02 | 0.02 | 0.02 | 0.02 |
| Onion powder | 3.00 | 3.00 | 3.00 | 3.00 | 3.00 | 3.00 | 3.00 |
| Cream flavour concentrate | 0.03 | 0.03 | 0.03 | 0.03 | 0.03 | 0.03 | 0.03 |
| Cheese flavouring | 0.03 | 0.03 | 0.03 | 0.03 | 0.03 | 0.03 | 0.03 |
| Tomato flavour concentrate | 0.04 | 0.04 | 0.04 | 0.04 | 0.04 | 0.04 | 0.04 |
| Spray-dried composition according to application example 2A | — | 2.00 | — | — | — | | |
| Spray-dried composition according to application example 2B | — | — | 2.00 | — | — | | |
| Spray-dried composition according to application example 2C | — | — | — | 2.00 | — | | |
| Spray-dried composition according to application example 2D | — | — | — | — | 2.00 | | |
| Spray-dried composition according to application example 2E | | | | | | 2.00 | |
| Spray-dried composition according to application example 2H | | | | | | | 2.00 |
| Total | 100 | 100 | 100 | 100 | 100 | 100 | 100 |

*not according to the invention 6 g of the spice mix was sprinkled on 94 g of potato crisps.

Application Example 16: Application in a Green Tea Drink

| | Usage in % w/w | |
|---|---|---|
| Ingredient | A | B |
| Green tea concentrate | 18.00 | 18.00 |
| 1% solution Ethyl-2-(4-hydroxy-3-methoxyphenyl) acetate (17) | 0.40 | — |
| 1% solution 3-phenylpropyl 2-(4-hydroxy-3-methoxyphenyl) acetate (22) | — | 0.015 |
| Demineralised water | 81.60 | 81.985 |
| Total | 100 | 100 |

The green tea concentrate is mixed with the 1% solution of ethyl-2-(4-hydroxy-3-methoxy-phenyl)acetate (17) in propylene glycol in the case of drink A, and with the 1% solution 3-phenylpropyl-2-(4-hydroxy-3-methoxyphenyl) acetate (22) in propylene glycol in the case of drink B. Subsequently, it is filled with demineralised water and mixed again thoroughly. The product is filtered afterwards, packaged ready-to-use, and sterilised at 118° C. The taste of the drinks A and B is evaluated by a panel of educated testers as clearly preferred to the non-flavoured green tea concentrate. The bitterness and the astringency is reduced by the addition of the compounds according to the invention.

Application Example 17: Use in an Ice Tea Beverage (Black Tea)

The esters of homovanillic acid were pre-dissolved in 10% or 1% ethanol, respectively. Black tea extract was dissolved in water and stirred together with sugar, a flavour preparation (peach taste), as well as the ethanol solutions of the esters of homovanillic acid in a beaker.

| | Usage in % w/w | | | |
|---|---|---|---|---|
| Ingredient | A | B | C | D |
| Black tea extract | 1.40 | 1.40 | 1.40 | 1.40 |
| Water | 89.5 | 89.51 | 89.51 | 89.515 |
| Flavour preparation (peach type) | 0.67 | 0.67 | 0.67 | 0.67 |
| Sugar | 7 | 7 | 7 | 7 |
| Citric acid (crystalline) | 1.20 | 1.20 | 1.20 | 1.20 |
| Ascorbic acid | 0.20 | 0.20 | 0.20 | 0.20 |
| 10% in ethanol Ethyl-2-(4-hydroxy-3-methoxyphenyl) acetate (17) | 0.03 | — | — | — |
| 10% in ethanol Propyl-2-(4-hydroxy-3-methoxyphenyl) acetate (18) | — | 0.02 | — | — |
| 1% in ethanol 3-phenylpropyl 2-(4-hydroxy-3-methoxyphenyl) acetate (22) | — | — | 0.02 | — |
| 1% in ethanol [(E)-cinnannyl]-2-(4-hydroxy-3-methoxyphenyl) acetate (2) | — | — | — | 0.015 |
| Total | 100 | 100 | 100 | 100 |

Application Example 18: Application in a Boullion

A=Reference preparation
B, C, D=Preparations according to the invention
All specifications are in % w/w.

| Ingredient | A* | B | C | D | E | F |
|---|---|---|---|---|---|---|
| Fat powder | 8.77 | 8.77 | 8.77 | 8.77 | 8.77 | 8.77 |
| Sodium glutamate | 8.77 | 8.77 | 8.77 | 8.77 | 8.77 | 8.77 |
| Yeast extract powder | 12.28 | 12.28 | 12.28 | 12.28 | 12.28 | 12.28 |
| Cooking salt | 29.83 | 29.83 | 29.83 | 29.83 | 29.83 | 29.83 |
| Maltodextrin | 37.28 | 36.68 | 36.98 | 36.88 | 37.265 | 37.27 |
| Natural vegetable extract | 3.07 | 3.07 | 3.07 | 3.07 | 3.07 | 3.07 |
| Ethyl-2-(4-hydroxy-3-methoxyphenyl) acetate (17) | — | 0.60 | — | — | — | — |
| Butyl-2-(4-hydroxy-3-methoxyphenyl) acetate (19) | — | — | 0.30 | — | — | — |
| Isobutyl-2-(4-hydroxy-3-methoxy-phenyl) acetate (9) | — | — | — | 0.40 | — | — |
| 3-phenylpropyl 2-(4-hydroxy-3-methoxyphenyl) acetate (22) | — | — | — | — | 0.015 | — |
| [(E)-cinnamyl]-2-(4-hydroxy-3-methoxyphenyl) acetate (2) | — | — | — | — | — | 0.01 |
| Total | 100 | 100 | 100 | 100 | 100 | 100 |

*not according to the invention
1,000 ml of hot water was poured onto 15 g of the respective powder mixture.

Application Example 19: Instant Soup, Type Leek Cream

A=Reference preparation
B, C, D, E=Preparations according to the invention
All specifications are in % w/w.

| Ingredient | A* | B | C | D | E | F | G |
|---|---|---|---|---|---|---|---|
| Potato starch | 20.00 | 20.00 | 20.00 | 20.00 | 20.00 | 20.00 | 20.00 |
| Fat powder | 25.00 | 25.00 | 25.00 | 25.00 | 25.00 | 25.00 | 25.00 |
| Lactose | 20.00 | 20.00 | 20.00 | 20.00 | 20.00 | 20.00 | 20.00 |
| Maltodextrin | 11.73 | 11.65 | 11.68 | 11.67 | 11.66 | 11.727 | 11.725 |
| Cooking salt | 8.00 | 8.00 | 8.00 | 8.00 | 8.00 | 8.00 | 8.00 |
| Sodium glutamate | 3.00 | 3.00 | 3.00 | 3.00 | 3.00 | 3.00 | 3.00 |
| Spinach powder | 2.00 | 2.00 | 2.00 | 2.00 | 2.00 | 2.00 | 2.00 |
| Green leek powder | 2.00 | 2.00 | 2.00 | 2.00 | 2.00 | 2.00 | 2.00 |
| Citric acid in powder form | 0.30 | 0.30 | 0.30 | 0.30 | 0.30 | 0.30 | 0.30 |
| Hardened vegetable fat | 3.00 | 3.00 | 3.00 | 3.00 | 3.00 | 3.00 | 3.00 |
| Freeze-dried leek | 1.00 | 1.00 | 1.00 | 1.00 | 1.00 | 1.00 | 1.00 |
| Chicken flavouring | 1.00 | 1.00 | 1.00 | 1.00 | 1.00 | 1.00 | 1.00 |
| Spice mix of "green leek powder" type | 2.00 | 2.00 | 2.00 | 2.00 | 2.00 | 2.00 | 2.00 |
| Spice mix of "cooked onion" type | 0.60 | 0.60 | 0.60 | 0.60 | 0.60 | 0.60 | 0.60 |
| Yeast spice mix of "vegetable stock powder" type | 0.30 | 0.30 | 0.30 | 0.30 | 0.30 | 0.30 | 0.30 |
| Turmeric extract | 0.07 | 0.07 | 0.07 | 0.07 | 0.07 | 0.07 | 0.07 |
| Ethyl-2-(4-hydroxy-3-methoxyphenyl) acetate (17) | — | 0.08 | — | — | 0.06 | | |
| Propyl-2-(4-hydroxy-3-methoxyphenyl) acetate (18) | — | — | 0.05 | — | — | | |
| Isobutyl-2-(4-hydroxy-3-methoxyphenyl) acetate (8) | — | — | — | 0.06 | 0.01 | | |
| 3-phenylpropyl 2-(4-hydroxy-3-methoxyphenyl) acetate (22) | | | | | | 0.003 | |
| [(E)-cinnamyl]-2-(4-hydroxy-3-methoxyphenyl) acetate (2) | | | | | | | 0.005 |
| Total | 100 | 100 | 100 | 100 | 100 | 100 | 100 |

100 ml of hot water was poured onto 5 g of the respective powder mixture to obtain a ready-to-eat soup.

Application Example 20: Instant Soup, Type Chicken Soup with Noodles

A=Reference preparation
B, C, D, E=Preparations according to the invention
All specifications are in % w/w.

| Ingredient | A* | B | C | D | E | F | G |
|---|---|---|---|---|---|---|---|
| Starch | 16.16 | 16.06 | 16.12 | 16.13 | 16.11 | 16.155 | 16.157 |
| Cooking salt | 7.00 | 7.00 | 7.00 | 7.00 | 7.00 | 7.00 | 7.00 |
| Refined saccharose | 3.20 | 3.20 | 3.20 | 3.20 | 3.20 | 3.20 | 3.20 |
| Sodium glutamate | 3.20 | 3.20 | 3.20 | 3.20 | 3.20 | 3.20 | 3.20 |
| Sodium inosinate/sodium guanylate in a ratio of 1:1 | 0.80 | 0.80 | 0.80 | 0.80 | 0.80 | 0.80 | 0.80 |
| Acid-hydrolysed vegetable protein | 8.00 | 8.00 | 8.00 | 8.00 | 8.00 | 8.00 | 8.00 |
| Fat powder | 2.00 | 2.00 | 2.00 | 2.00 | 2.00 | 2.00 | 2.00 |
| Spray-dried vegetable fat | 1.00 | 1.00 | 1.00 | 1.00 | 1.00 | 1.00 | 1.00 |
| Freeze-dried chicken meat in pieces | 2.00 | 2.00 | 2.00 | 2.00 | 2.00 | 2.00 | 2.00 |
| Soup noodles | 32.00 | 32.00 | 32.00 | 32.00 | 32.00 | 32.00 | 32.00 |
| Maltodextrin | 12.00 | 12.00 | 12.00 | 12.00 | 12.00 | 12.00 | 12.00 |
| Freeze-dried Chinese vegetables | 4.60 | 4.60 | 4.60 | 4.60 | 4.60 | 4.60 | 4.60 |
| Chicken flavouring | 8.00 | 8.00 | 8.00 | 8.00 | 8.00 | 8.00 | 8.00 |
| Food dye riboflavin | 0.04 | 0.04 | 0.04 | 0.04 | 0.04 | 0.04 | 0.04 |
| Ethyl-2-(4-hydroxy-3-methoxyphenyl) acetate (17) | — | 0.10 | — | — | 0.04 | — | — |
| Butyl-2-(4-hydroxy-3-methoxyphenyl) acetate (19) | — | — | 0.04 | — | 0.01 | — | — |
| Hexyl-2-(4-hydroxy-3-methoxyphenyl) acetate (21) | — | — | — | 0.031 | — | — | — |
| 3-phenylpropyl 2-(4-hydroxy-3-methoxyphenyl) acetate (22) | — | — | — | — | — | 0.005 | — |
| [(E)-cinnamyl]-2-(4-hydroxy-3-methoxyphenyl) acetate (2) | — | — | — | — | — | — | 0.003 |
| Total | 100 | 100 | 100 | 100 | 100 | 100 | 100 |

*not according to the invention 4.60 g of the respective powder mixture was boiled in 100 ml of water for 10 minutes to obtain a ready-to-eat soup.

Application Example 21: Preparation of Dark Chilli Chocolates Using the Substances According to the Invention All specifications in % w/w, unless specified otherwise.
A=Dark chocolate reference preparation
B=Calorie-reduced dark chocolate
C=Calorie-reduced dark chocolate
D=Calorie-reduced dark chocolate
E=Calorie-reduced whole milk chocolate
F=Dark chocolate
G=Dark chocolate

| Ingredient | A* | B | C | D | E | F | G |
|---|---|---|---|---|---|---|---|
| Cocoa butter | 14.49 | 12.99 | 13.49 | 9.48 | 14.00 | 14.49 | 14.50 |
| Cocoa paste | 41.00 | 39.00 | 42.00 | 44.00 | 23.00 | 41.00 | 41.00 |
| Erythritol | — | 47.45 | — | — | — | — | — |
| Crystalline maltitol | — | — | — | 23.00 | — | — | — |
| Inulin | — | — | — | 23.00 | — | — | — |
| Sorbitol | — | — | 44.00 | — | — | — | — |
| Lactitol | — | — | — | — | 38.55 | — | — |
| Polydextrose | — | — | — | — | 9.70 | — | — |
| Whole milk powder | — | — | — | — | 14.00 | — | — |
| Sucrose | 43.98 | — | — | — | — | 44.00 | 44.00 |
| Lecithin | 0.48 | 0.48 | 0.40 | 0.48 | 0.50 | 0.48 | 0.48 |
| Vanillin | 0.02 | 0.02 | 0.02 | 0.02 | 0.20 | 0.02 | 0.02 |
| Aspartame | — | 0.03 | 0.06 | — | 0.03 | — | — |

-continued

| Ingredient | A* | B | C | D | E | F | G |
|---|---|---|---|---|---|---|---|
| Capsicum extract (1,000,000 SHU) | 0.03 | 0.02 | 0.02 | 0.01 | — | 0.01 | — |
| Hexyl-2-(4-hydroxy-3-methoxyphenyl) acetate (21) | — | 0.01 | — | 0.01 | 0.01 | — | — |
| Butyl-2-(4-hydroxy-3-methoxyphenyl) acetate (19) | — | — | 0.01 | — | 0.01 | — | — |
| 3-phenylpropyl 2-(4-hydroxy-3-methoxyphenyl) acetate (22) | — | — | — | — | — | 0.001 | — |
| [(E)-cinnamyl]-2-(4-hydroxy-3-methoxyphenyl) acetate (2) | — | — | — | — | — | — | 0.002 |
| Total | 100 | 100 | 100 | 100 | 100 | 100 | 100 |

*not according to the invention

The effects found in the above application examples can be transferred to all products of the respective product category, i.e. particularly to toothpastes, chewing gums, mouthwashes, lozenges, gelatine capsules, chewing sweets and tea in bags, if applicable by modifications which can be easily carried out by a person skilled in the art. For the person skilled in the art, it is readily apparent on the basis of the present description that the compounds and mixtures according to the invention can easily be interchanged with one another maybe with minor modifications. This means that the compound according to the invention used in the products of the application examples must also be regarded as a placeholder for the other compounds and mixtures according to the invention. Also the concentration of the used compound or mixture according to the invention is adjustable as can be easily recognised by a person skilled in the art. In addition, the other product-specific components in the respective application example can also easily be interchanged with or supplemented by further product-specific components as can be easily understood by the person skilled in the art. A variety of such product-specific components are disclosed in the above description.

The invention claimed is:

1. A method for imparting a warm and/or pungent taste sensation, the method comprising:
    adding 5 to 1,000 mg/kg of one or more compounds of formula (I), or physiologically acceptable salt thereof, to a preparation that comes into contact with an oral cavity, wherein the compounds of formula (I) are represented by the following structure:

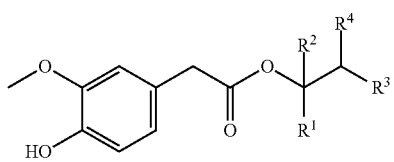

(I)

wherein
(i) $R^1$ and $R^2$ represent, independently of each other, a hydrogen atom or an alkyl residue with 1-2 carbon atoms, and
    $R^3$ and $R^4$ represent, independently of each other, a hydrogen atom or a linear or branched alkyl residue with 1 to 5 carbon atoms, a phenyl residue, an alkylphenyl residue or a phenylalkyl residue or a linear or branched alkenyl residue with 2 to 4 carbon atoms or an alkenylphenyl residue or a phenylalkenyl residue; or (ii) $R^1$ and $R^3$ along with the carbon atoms linking them form a cyclohexyl ring,
    $R^2$ represents a hydrogen atom or an alkyl residue with 1-2 carbon atoms,
    $R^4$ represents a hydrogen atom or a linear or branched alkyl residue with 1 to 5 carbon atoms, a phenyl residue, an alkylphenyl residue or a phenylalkyl residue or a linear or branched alkenyl residue with 2 to 4 carbon atoms or an alkenylphenyl residue or a phenylalkenyl residue,
    wherein the one or more compounds in accordance with formula I being one or several different compounds of formula (I), and/or physiologically acceptable salts thereof, where the phenolic hydroxy group in formula (I) is deprotonated, respectively.

2. The method of claim 1, wherein one or more of the compounds of formula (I), independently of each other, have $R^1$ and $R^2$ being, independently of each other, a hydrogen atom or methyl group, $R^3$ and $R^4$ being, independently of each other, a hydrogen atom or a linear or branched alkyl residue with 1 to 5 carbon atoms or a phenyl residue, an alkylphenyl residue or a phenylalkyl residue or an alkenylphenyl residue or a phenylalkenyl residue.

3. The method of claim 1, wherein one or more of the compounds of formula (I), independently of each other, are represented by the following structure for Formula (Ia)

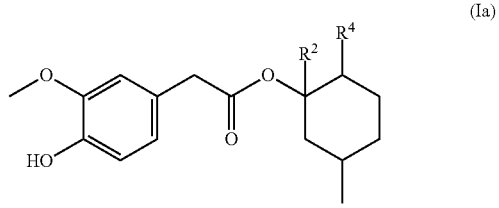

(Ia)

wherein $R^2$ is a hydrogen atom and $R^4$ is 2-propyl.

4. The method of claim 1, wherein one or more of the compounds of formula (I), independently of each other, have:
    $R^1$ and $R^2$ being a hydrogen atom, respectively,
    $R^3$ being a hydrogen atom or a linear or branched alkyl residue with 1 to 4 carbon atoms or a phenyl residue, an alkylphenyl residue or a phenylalkyl residue or an alkenylphenyl residue or a phenylalkenyl residue, $R^4$ being a hydrogen atom.

5. The method of claim 1, wherein the one or more compounds of formula (I) are selected from:

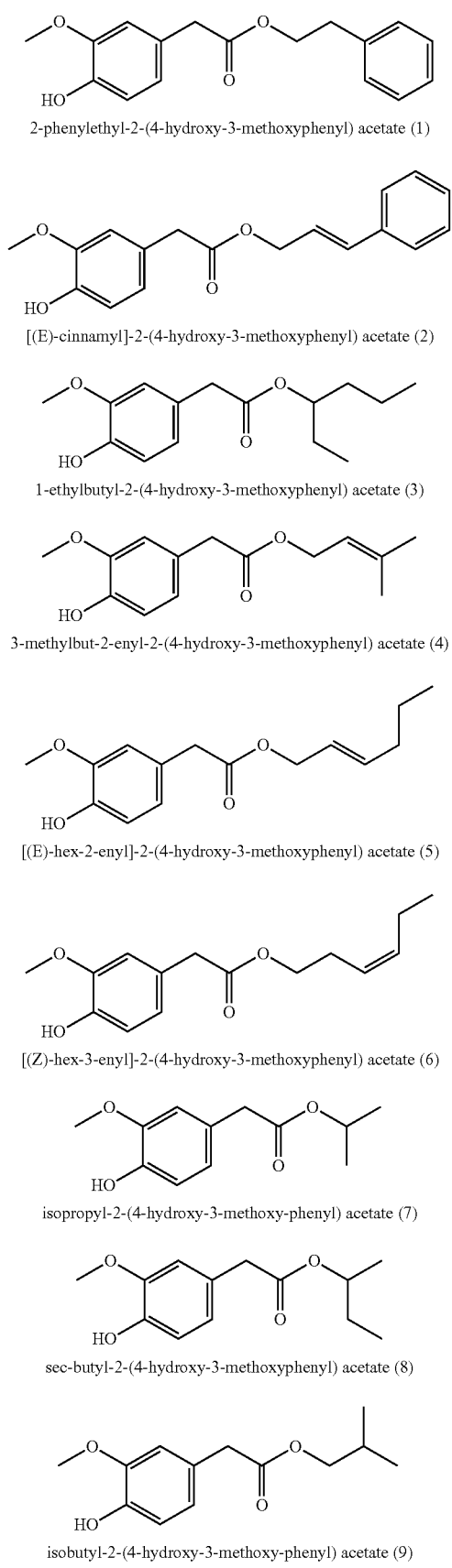
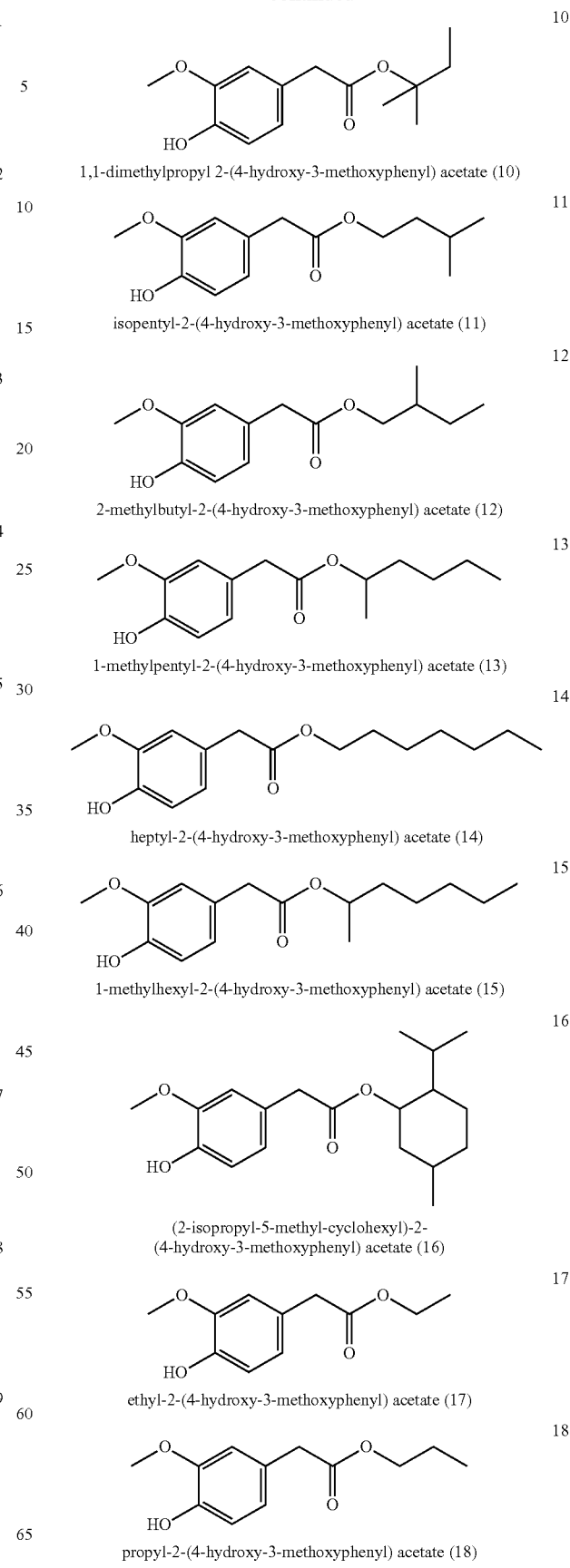

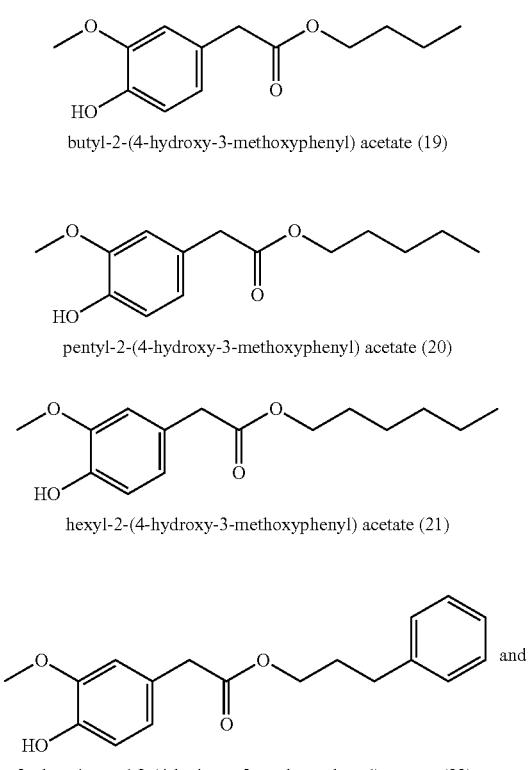

butyl-2-(4-hydroxy-3-methoxyphenyl) acetate (19)

pentyl-2-(4-hydroxy-3-methoxyphenyl) acetate (20)

hexyl-2-(4-hydroxy-3-methoxyphenyl) acetate (21)

3-phenylpropyl 2-(4-hydroxy-3-methoxyphenyl) acetate (22) and 4-phenylbutyl 2-(4-hydroxy-3-methoxyphenyl) acetate (23).

6. The method of claim 1, wherein the one or more compounds of formula (I) are selected from:

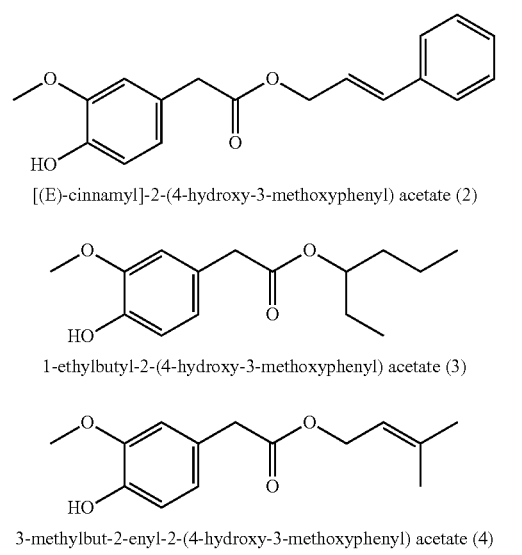

[(E)-cinnamyl]-2-(4-hydroxy-3-methoxyphenyl) acetate (2)

1-ethylbutyl-2-(4-hydroxy-3-methoxyphenyl) acetate (3)

3-methylbut-2-enyl-2-(4-hydroxy-3-methoxyphenyl) acetate (4)

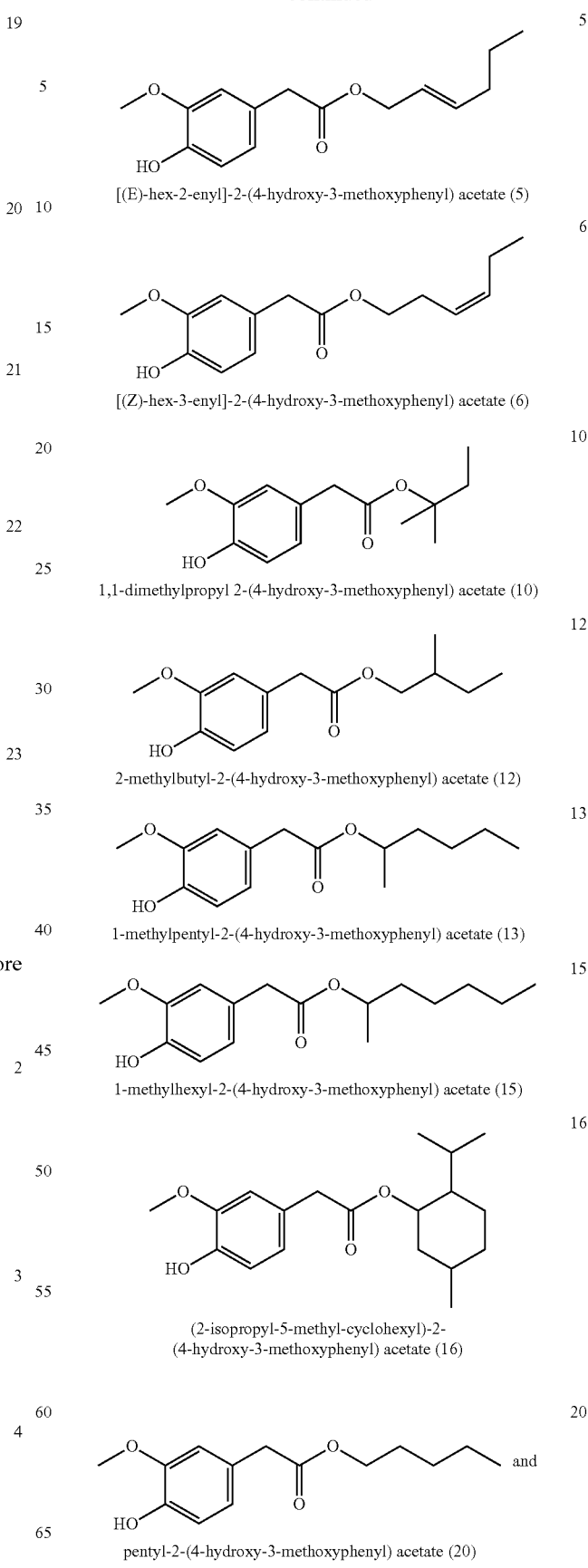

[(E)-hex-2-enyl]-2-(4-hydroxy-3-methoxyphenyl) acetate (5)

[(Z)-hex-3-enyl]-2-(4-hydroxy-3-methoxyphenyl) acetate (6)

1,1-dimethylpropyl 2-(4-hydroxy-3-methoxyphenyl) acetate (10)

2-methylbutyl-2-(4-hydroxy-3-methoxyphenyl) acetate (12)

1-methylpentyl-2-(4-hydroxy-3-methoxyphenyl) acetate (13)

1-methylhexyl-2-(4-hydroxy-3-methoxyphenyl) acetate (15)

(2-isopropyl-5-methyl-cyclohexyl)-2-(4-hydroxy-3-methoxyphenyl) acetate (16)

pentyl-2-(4-hydroxy-3-methoxyphenyl) acetate (20) and

-continued

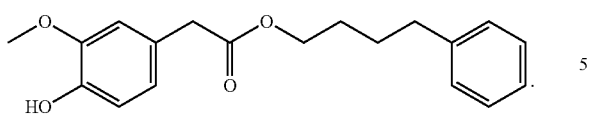

4-phenylbutyl 2-(4-hydroxy-3-methoxyphenyl) acetate (23)

7. The method of claim 1, wherein the one or more compounds of formula (I) includes:
1 ethyl-2-(4-hydroxy-3-methoxyphenyl) acetate (17)

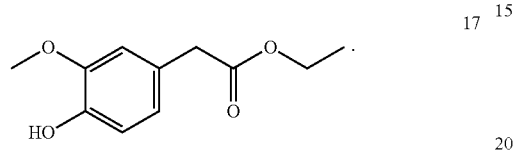

8. The method of claim 1 comprising adding 5 to 500 mg/kg of the one or more compounds of formula (I), or physiologically acceptable salt thereof.

9. A method for imparting a warm and/or pungent taste sensation to a preparation that comes into contact with an oral cavity, the method comprising adding 5 to 500 mg/kg of ethyl-2-(4-hydroxy-3-methoxyphenyl) acetate (17) to the preparation:

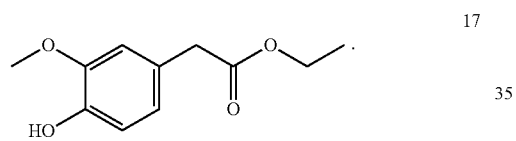

10. A method for imparting a warm and/or pungent taste sensation to a preparation that comes into contact with an oral cavity, the method comprising:
(a) adding 5 to 1,000 mg/kg of ethyl-2-(4-hydroxy-3-methoxyphenyl) acetate (17) to the preparation:

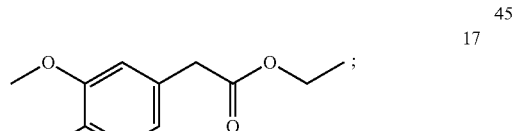

and
(b) adding at least one further compound selected from the group consisting of

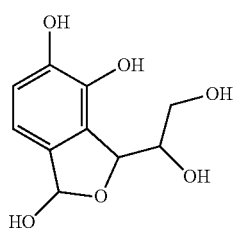

3-(1,2-dihydroxyethyl)-1,3-dihydroiso-benzofuran-1,4,5-triol

-continued

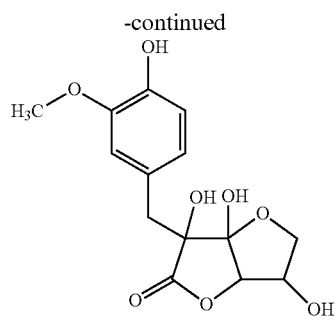

6-[(3-hydroperoxy-4-hydroxyphenyl)-methyl]-3,6,6a-trihydroxy-3,3a-dihydro-2H-furo[3,2-b]furan-5-one

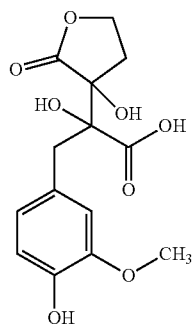

2-hydroxy-3-(4-hydroxy-3-methoxyphenyl)-2-(3-hydroxy-2-oxo-tetrahydrofuran-3-yl) propanoic acid

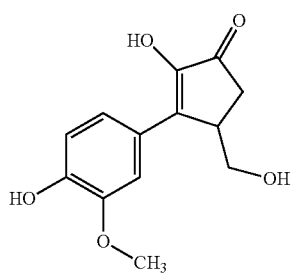

2-hydroxy-3-(4-hydroxy-3-methoxyphenyl)-4-(hydroxymethyl) cyclopent-2-en-1-one

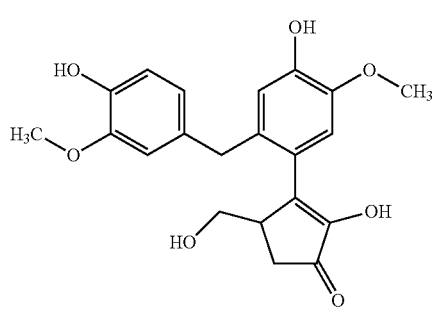

2-hydroxy-3-[4-hydroxy-2-[(4-hydroxy-3-methoxyphenyl)methyl]-5-methoxyphenyl]-4-(hydroxymethyl) cyclopent-2-en-1-one

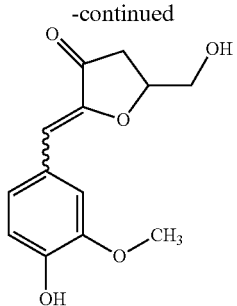

2-[(4-hydroxy-3-methoxyphenyl)-methylene]-5-(hydroxymethyl) tetrahydrofuran-3-one

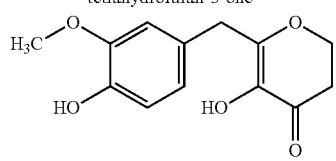

5-hydroxy-6-[(4-hydroxy-3-methoxyphenyl)methyl]-2,3-dihydropyran-4-one

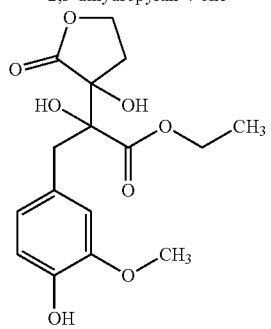

Ethyl-2-hydroxy-3-(4-hydroxy-3-methoxyphenyl)-2-(3-hydroxy-2-oxo-tetrahydro-furan-3-yl) propanoate

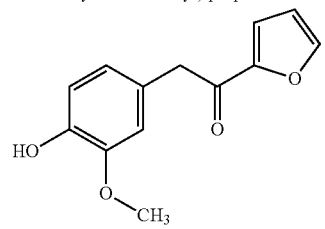

1-(2-furyl)-2-(4-hydroxy-3-methoxyphenyl) ethanone

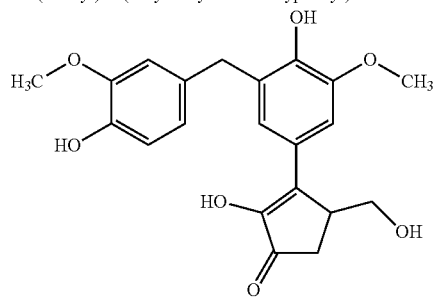

2-hydroxy-3-[4-hydroxy-3-[(4-hydroxy-3-methoxyphenyl)methyl]-5-methoxyphenyl]-4-(hydroxymethyl) cyclopent-2-en-1-one

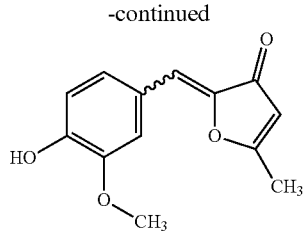

2-[(4-hydroxy-3-methoxyphenyl)methylene]-5-methyl furan-3-one

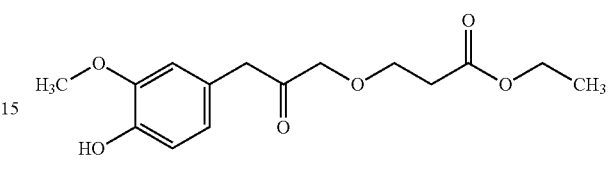

Ethyl-3-[3-(4-hydroxy-3-methoxyphenyl)-2-oxo-propoxy] propanoate

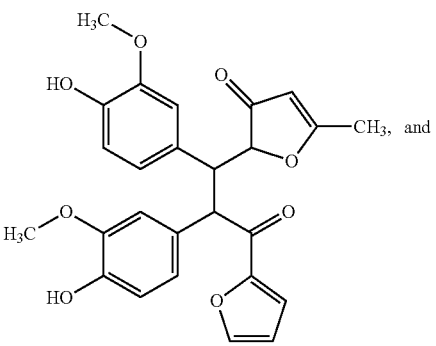

2-[3-(2-furyl)-1,2-bis(4-hydroxy-3-methoxyphenyl)-3-oxo-propyl]-5-methyl furan-3-one

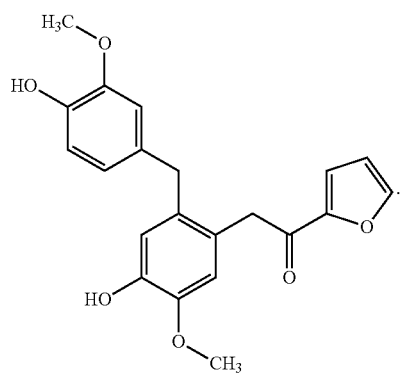

1-(2-furyl)-2-[4-hydroxy-2-[(4-hydroxy-3-methoxyphenyl)methyl]-5-methoxy-phenyl] ethanone

11. The method of claim 1, wherein the preparation is not a wine or a wine cocktail.

12. The method of claim 1, wherein the preparation does not comprise ethanol.

* * * * *